(12) United States Patent
Hartman et al.

(10) Patent No.: US 7,052,848 B2
(45) Date of Patent: May 30, 2006

(54) INTERNAL POSITIVE CONTROL FOR PROBE-BASED NUCLEIC ACID MOLECULE ASSAYS AND METHODS OF MAKING AND USING THEREOF

(75) Inventors: Laurie J. Hartman, Germantown, MD (US); David A. Norwood, Jr., Thurmont, MD (US); Leonard P. Wasieloski, Jr., Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 59 days.

(21) Appl. No.: 11/018,377

(22) Filed: Dec. 22, 2004

(65) Prior Publication Data

US 2005/0095644 A1    May 5, 2005

Related U.S. Application Data

(63) Continuation-in-part of application No. 10/376,323, filed on Mar. 3, 2003.

(60) Provisional application No. 60/361,455, filed on Mar. 4, 2002.

(51) Int. Cl.
    *C12Q 1/68* (2006.01)
(52) U.S. Cl. .......................................................... 435/6
(58) Field of Classification Search .................... 435/6, 435/91.1, 91.2
    See application file for complete search history.

(56) References Cited

U.S. PATENT DOCUMENTS 5,723,591 A    3/1998   Livak et al.
5,952,202 A    9/1999   Aoyagi et al.
6,312,930 B1   11/2001  Tice, Jr. et al.

FOREIGN PATENT DOCUMENTS

WO    WO 00/29613     5/2000
WO    WO 03/075837    9/2003

OTHER PUBLICATIONS

Courtney, et al. (1999) "Development of Internal Controls for Probe-Based Nucleic Acid Diagnostic Assays" Anal. Biochem. 270(2):249-256.
Hartman, et al. (2005) "Development of a Novel Internal Positive Control for Taqman Based Assays" Mol. Cell. Probes 19:51-59.
Ho, et al. (1998) "Site-Directed Mutagenesis by Overlap Extension Using the Polymerase Chain Reaction" Gene 77(1):51-59.
Ursi, et al. (1998) "Construction of an Internal Control for the Detection of Chlamydia pneumoniae by PCR" Mol. Cell. Probes 12:235-238.

Primary Examiner—Jeffrey Fredman
Assistant Examiner—Heather G. Calamita
(74) Attorney, Agent, or Firm—Elizabeth Arwine

(57) ABSTRACT

Disclosed herein are isolated nucleic acid molecules that may be used as an internal positive controls in probe-based nucleic acid assays such as TaqMan® based assays. Also disclosed are probes comprising the isolated nucleic acid molecule of the present invention. The probes may comprise a reporter molecule and a quencher molecule. Also disclosed are assays which comprise using the probe of the present invention. The probes may be used to distinguish false negative results from true negative results in assays for a target nucleic acid molecule. The probe may be used in conjunction with probe-based nucleic acid assays for the detection of an organism such as one belonging to *Bacillus*, *Mycobacterium*, *Francisella*, *Brucella*, *Clostridium*, *Yersinia*, *Variola*, *Orthopox*, or *Burkholderia*.

21 Claims, 12 Drawing Sheets

Figure 2

Figure 1:
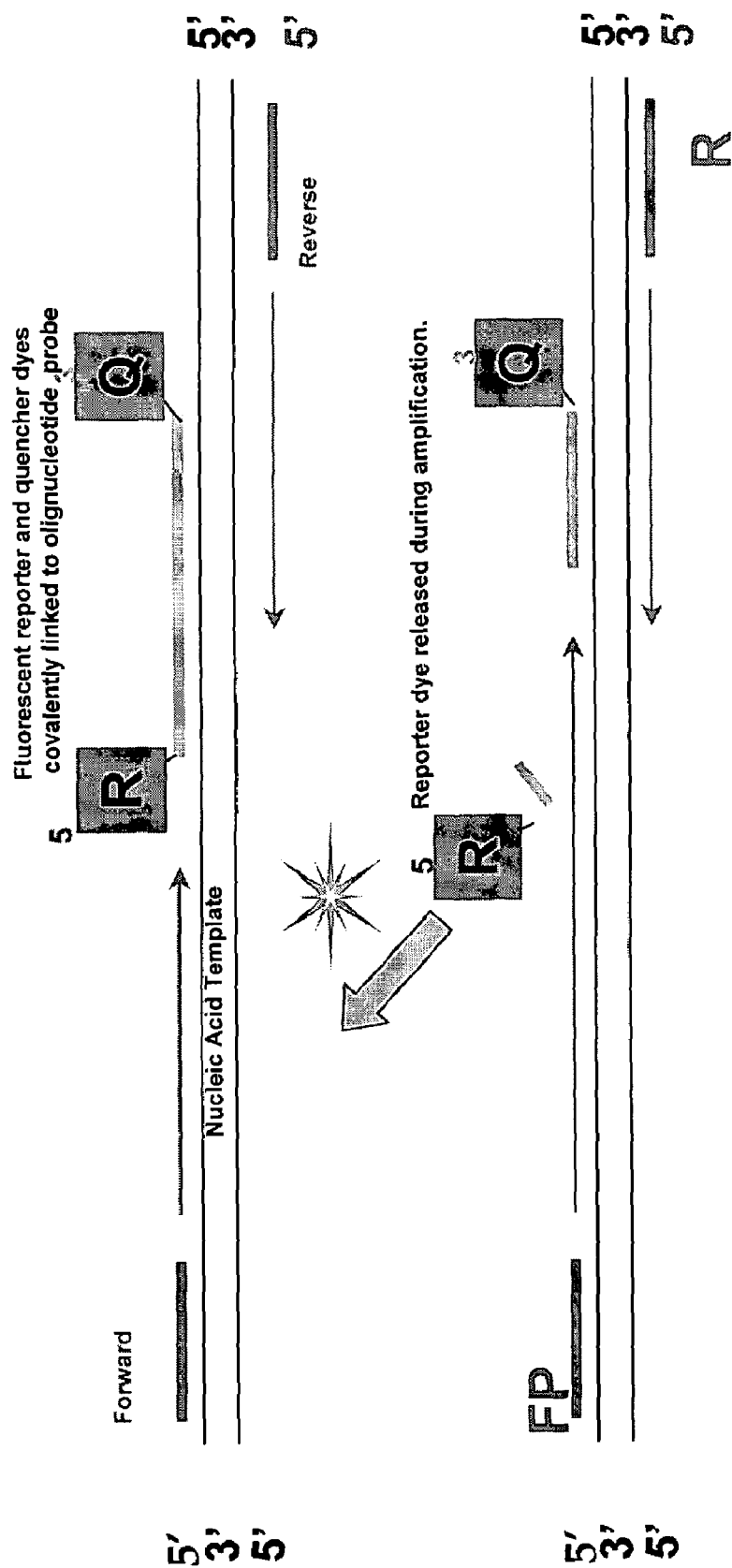

SEQUENCE LISTING

<160> NUMBER OF SEQ ID NOS: 91

<210> SEQ ID NO 1
<211> LENGTH: 153
<212> TYPE: DNA
<213> ORGANISM: Artificial
<220> FEATURE:
<223> OTHER INFORMATION: Bacillus anthracis Protective Antigen

<400> SEQUENCE: 1
ttcaagttgt actggaccga ttctcaaaat aaaaagaag tgatttctag tgataactta      60
caattgccag aattaaaaca aaaatcttcg aactcaagaa aaaagcgaag tacaagtgct     120
ggacctacgg ttccagaccg tgacaatgat gga                                 153

<210> SEQ ID NO 2
<211> LENGTH: 25
<212> TYPE: DNA

```
<213> ORGANISM: Artificial
<220> FEATURE:
<223> OTHER INFORMATION: Upper Primer: IPC3L

<400> SEQUENCE: 2
cgttgttacc gactggatta ttacc                                              25

<210> SEQ ID NO 3
<211> LENGTH: 21
<212> TYPE: DNA
<213> ORGANISM: Artificial
<220> FEATURE:
<223> OTHER INFORMATION: Lower Primer: IPC5U

<400> SEQUENCE: 3
tccgcatacc agttgttgtc g                                                  21

<210> SEQ ID NO 4
<211> LENGTH: 28
<212> TYPE: DNA
<213> ORGANISM: Artificial
<220> FEATURE:
<223> OTHER INFORMATION: Probe: IPCP35F

<400> SEQUENCE: 4
cgtagttgat cgctctcagt ccatccgt                                           28

<210> SEQ ID NO 5
<211> LENGTH: 25
<212> TYPE: DNA
<213> ORGANISM: Artificial
<220> FEATURE:
<223> OTHER INFORMATION: Upper Primer: BAPA3U

<400> SEQUENCE: 5
ttcaagttgt actggaccga ttctc                                              25

<210> SEQ ID NO 6
<211> LENGTH: 21
<212> TYPE: DNA
<213> ORGANISM: Artificial
<220> FEATURE:
<223> OTHER INFORMATION: Lower Primer: BAPA5L

<400> SEQUENCE: 6
tccatcattg tcacggtctg g                                                  21

<210> SEQ ID NO 7
<211> LENGTH: 28
<212> TYPE: DNA
<213> ORGANISM: Artificial
<220> FEATURE:
<223> OTHER INFORMATION: Probe: BAPA3P2A

<400> SEQUENCE: 7
ccgtaggtcc agcacttgta cttcgctt                                           28

<210> SEQ ID NO 8
<211> LENGTH: 22
<212> TYPE: DNA
<213> ORGANISM: Artificial
<220> FEATURE:
<223> OTHER INFORMATION: BANPAIS1

<400> SEQUENCE: 8
gtaacaatgt gggtagatga cc                                                 22
```

<210> SEQ ID NO 9
<211> LENGTH: 28
<212> TYPE: DNA
<213> ORGANISM: Artificial
<220> FEATURE:
<223> OTHER INFORMATION: PA35PC1L

<400> SEQUENCE: 9
tctcagtcca tccgtttttc ttgagttc                                    28

<210> SEQ ID NO 10
<211> LENGTH: 252
<212> TYPE: DNA
<213> ORGANISM: Artificial
<220> FEATURE:
<223> OTHER INFORMATION: Fragment 1

<400> SEQUENCE: 10
gtaacaatgt gggtagatga ccaagaagtg attaataaag cttctaattc taacaaaatc    60
agattagaaa aaggaagatt atatcaaata aaaattcaat atcaacgaga aaatcctact   120
gaaaaaggat tggatttcaa gttgtactgg accgattctc aaaataaaaa agaagtgatt   180
tctagtgata acttacaatt gccagaatta aaacaaaaat cttcgaactc aagaaaaacg   240
gatggactga ga                                                      252

<210> SEQ ID NO 11
<211> LENGTH: 22
<212> TYPE: DNA
<213> ORGANISM: Artificial
<220> FEATURE:
<223> OTHER INFORMATION: BANPAIA1

<400> SEQUENCE: 11
cttatcaatc cgtcctgtaa cc                                           22

<210> SEQ ID NO 12
<211> LENGTH: 25
<212> TYPE: DNA
<213> ORGANISM: Artificial
<220> FEATURE:
<223> OTHER INFORMATION: PA35PC1U

<400> SEQUENCE: 12
gcgatcaact acgttccaga ccgtg                                        25

<210> SEQ ID NO 13
<211> LENGTH: 225
<212> TYPE: DNA
<213> ORGANISM: Artificial
<220> FEATURE:
<223> OTHER INFORMATION: Fragment 2

<400> SEQUENCE: 13
gcgatcaact acgttccaga ccgtgacaat gatggaatcc ctgattcatt agaggtagaa    60
ggatatacgg ttgatgtcaa aaataaaaga acttttcttt caccatggat ttctaatatt   120
catgaaaaga aaggattaac caaatataaa tcatctcctg aaaaatggag cacggcttct   180
gatccgtaca gtgatttcga aaaggttaca ggacggattg ataag                  225

<210> SEQ ID NO 14
<211> LENGTH: 22
<212> TYPE: DNA

```
<213> ORGANISM: Artificial
<220> FEATURE:
<223> OTHER INFORMATION: BANPAIS1

<400> SEQUENCE: 14
gtaacaatgt gggtagatga cc                                              22

<210> SEQ ID NO 15
<211> LENGTH: 28
<212> TYPE: DNA
<213> ORGANISM: Artificial
<220> FEATURE:
<223> OTHER INFORMATION: PA35PC2L

<400> SEQUENCE: 15
cgtagttgat cgctctcagt ccatccgt                                        28

<210> SEQ ID NO 16
<211> LENGTH: 265
<212> TYPE: DNA
<213> ORGANISM: Artificial
<220> FEATURE:
<223> OTHER INFORMATION: Fragment 3

<400> SEQUENCE: 16
gtaacaatgt gggtagatga ccaagaagtg attaataaag cttctaattc taacaaaatc     60
agattagaaa aaggaagatt atatcaaata aaaattcaat atcaacgaga aaatcctact    120
gaaaaaggat tggatttcaa gttgtactgg accgattctc aaaataaaaa agaagtgatt    180
tctagtgata acttacaatt gccagaatta aaacaaaaat cttcgaactc aagaaaaacg    240
gatggactga gagcgatcaa ctacg                                          265

<210> SEQ ID NO 17
<211> LENGTH: 22
<212> TYPE: DNA
<213> ORGANISM: Artificial
<220> FEATURE:
<223> OTHER INFORMATION: BANPAIA1

<400> SEQUENCE: 17
cttatcaatc cgtcctgtaa cc                                              22

<210> SEQ ID NO 18
<211> LENGTH: 28
<212> TYPE: DNA
<213> ORGANISM: Artificial
<220> FEATURE:
<223> OTHER INFORMATION: PA35PC2U

<400> SEQUENCE: 18
acggatggac tgagagcgat caactacg                                        28

<210> SEQ ID NO 19
<211> LENGTH: 240
<212> TYPE: DNA
<213> ORGANISM: Artificial
<220> FEATURE:
<223> OTHER INFORMATION: Fragment 4

<400> SEQUENCE: 19
acggatggac tgagagcgat caactacgtt ccagaccgtg acaatgatgg aatccctgat     60
tcattagagg tagaaggata tacggttgat gtcaaaaata aagaactttt ctttcacca    120 tggatttcta atattcatga aagaaaggga ttaaccaaat ataaatcatc tcctgaaaaa    180
```

```
tggagcacgg cttctgatcc gtacagtgat ttcgaaaagg ttacaggacg gattgataag    240
```

```
<210> SEQ ID NO 20
<211> LENGTH: 25
<212> TYPE: DNA
<213> ORGANISM: Artificial
<220> FEATURE:
<223> OTHER INFORMATION: BANPABIS1

<400> SEQUENCE: 20
caacgagaaa atcctactga aaaag                                          25

<210> SEQ ID NO 21
<211> LENGTH: 24
<212> TYPE: DNA
<213> ORGANISM: Artificial
<220> FEATURE:
<223> OTHER INFORMATION: BANPABIA1

<400> SEQUENCE: 21
gaaatcactg tacggatcag aagc                                           24

<210> SEQ ID NO 22
<211> LENGTH: 348
<212> TYPE: DNA
<213> ORGANISM: Artificial
<220> FEATURE:
<223> OTHER INFORMATION: Fragment 5

<400> SEQUENCE: 22
caacgagaaa atcctactga aaaggattg gatttcaagt tgtactggac cgattctcaa    60
aataaaaaag aagtgatttc tagtgataac ttacaattgc cagaattaaa acaaaaatct   120
tcgaactcaa gaaaacgga tggactgaga gcgatcaact acgttccaga ccgtgacaat   180
gatggaatcc ctgattcatt agaggtagaa ggatatacgg ttgatgtcaa aaataaaaga   240
acttttcttt caccatggat ttctaatatt catgaaaaga aggattaac caaatataaa     300 tcatctcctg aaaaatggag cacggcttct gatccgtaca gtgatttc                348

<210> SEQ ID NO 23
<211> LENGTH: 521
<212> TYPE: DNA
<213> ORGANISM: Artificial
<220> FEATURE:
<223> OTHER INFORMATION: Clone 11

<400> SEQUENCE: 23
gaaacagcta tgaccatgat tacgccaagc ttggtaccga gctcggatcc actagtaacg    60
gccgccagtg tgctggaatt cggcttcaac gagaaaatcc tactgaaaaa ggattggatt   120
tcaagttgta ctggaccgat tctcaaaata aaaagaagt gatttctagt gataacttac    180
aattgccaga attaaaacaa aaatcttcga actcaagaaa acggatgga ctgagagcga    240 tcaactacgt tccagaccgt gacaatgatg gaatccctga ttcattagag gtagaaggat   300
atacggttga tgtcaaaaat aaaagaactt tctttcacc atggatttct aatattcatg    360
aaaagaaagg attaaccaaa tataaatcat ctcccgaaaa atggagcacg gcttctgatc   420
cgtacagtga tttcaagccg aattctgcag atatccatca cactggcggc cgctcgagca   480
tgcatctaga gggcccaatt cgccctatag tgagtcgtat t                        521

<210> SEQ ID NO 24
```

```
<211> LENGTH: 25
<212> TYPE: DNA
<213> ORGANISM: Artificial
<220> FEATURE:
<223> OTHER INFORMATION: MOD31L

<400> SEQUENCE: 24
tcggtaacaa cgatccaatc ctttt                                           25

<210> SEQ ID NO 25
<211> LENGTH: 18
<212> TYPE: DNA
<213> ORGANISM: Artificial
<220> FEATURE:
<223> OTHER INFORMATION: PCR II FOR

<400> SEQUENCE: 25
caggaaacag ctatgacc                                                   18

<210> SEQ ID NO 26
<211> LENGTH: 134
<212> TYPE: DNA
<213> ORGANISM: Artificial
<220> FEATURE:
<223> OTHER INFORMATION: Fragment 6

<400> SEQUENCE: 26
caggaaacag ctatgaccat gattacgcca agcttggtac cgagctcgga tccactagta     60
acggccgcca gtgtgctgga attcggcttc aacgagaaaa tcctactgaa aaaggattgg    120
atcgttgtta ccga                                                      134

<210> SEQ ID NO 27
<211> LENGTH: 25
<212> TYPE: DNA
<213> ORGANISM: Artificial
<220> FEATURE:
<223> OTHER INFORMATION: MOD31U

<400> SEQUENCE: 27
ctggattatt accaaaataa aaaag                                           25

<210> SEQ ID NO 28
<211> LENGTH: 18
<212> TYPE: DNA
<213> ORGANISM: Artificial
<220> FEATURE:
<223> OTHER INFORMATION: PCR II REV

<400> SEQUENCE: 28
tgtaaaacga cggccagt                                                   18

<210> SEQ ID NO 29
<211> LENGTH: 415
<212> TYPE: DNA
<213> ORGANISM: Artificial
<220> FEATURE:
<223> OTHER INFORMATION: Fragment 7

<400> SEQUENCE: 29
ctggattatt accaaaataa aaaagaagtg atttctagtg ataacttaca attgccagaa     60
ttaaaacaaa aatcttcgaa ctcaagaaaa acggatggac tgagagcgat caactacgtt    120
ccagaccgtg acaatgatgg aatccctgat tcattagagg tagaaggata tacggttgat    180
gtcaaaaata aagaacttt tctttcacca tggatttcta atattcatga aagaaagga     240
```

```
ttaaccaaat ataaatcatc tcctgaaaaa tggagcacgg cttctgatcc gtacagtgat      300
ttcaagccga attctgcaga tatccatcac actggcggcc gctcgagcat gcatctagag      360
ggcccaattc gccctatagt gagtcgtatt acaattcact ggccgtcgtt ttaca           415
```

<210> SEQ ID NO 30
<211> LENGTH: 25
<212> TYPE: DNA
<213> ORGANISM: Artificial
<220> FEATURE:
<223> OTHER INFORMATION: MOD32L

<400> SEQUENCE: 30

```
ggtaataatc cagtcggtaa caacg                                             25
```

<210> SEQ ID NO 31
<211> LENGTH: 18
<212> TYPE: DNA
<213> ORGANISM: Artificial
<220> FEATURE:
<223> OTHER INFORMATION: PCR II FOR

<400> SEQUENCE: 31

```
caggaaacag ctatgacc                                                     18
```

<210> SEQ ID NO 32
<211> LENGTH: 147
<212> TYPE: DNA
<213> ORGANISM: Artificial
<220> FEATURE:
<223> OTHER INFORMATION: Fragment 8

<400> SEQUENCE: 32

```
caggaaacag ctatgaccat gattacgcca agcttggtac cgagctcgga tccactagta       60
acggccgcca gtgtgctgga attcggcttc aacgagaaaa tcctactgaa aaaggattgg      120
atcgttgtta ccgactggat tattacc                                          147
```

<210> SEQ ID NO 33
<211> LENGTH: 25
<212> TYPE: DNA
<213> ORGANISM: Artificial
<220> FEATURE:
<223> OTHER INFORMATION: MOD32U

<400> SEQUENCE: 33

```
cgttgttacc gactggatta ttacc                                             25
```

<210> SEQ ID NO 34
<211> LENGTH: 18
<212> TYPE: DNA
<213> ORGANISM: Artificial
<220> FEATURE:
<223> OTHER INFORMATION: PCR II REV

<400> SEQUENCE: 34

```
tgtaaaacga cggccagt                                                     18
```

<210> SEQ ID NO 35
<211> LENGTH: 427
<212> TYPE: DNA
<213> ORGANISM: Artificial
<220> FEATURE:
<223> OTHER INFORMATION: Fragment 9

```
<400> SEQUENCE: 35
cgttgttacc gactggatta ttaccaaaat aaaaagaag tgatttctag tgataactta      60
caattgccag aattaaaaca aaaatcttcg aactcaagaa aaacggatgg actgagagcg    120
atcaactacg ttccagaccg tgacaatgat ggaatccctg attcattaga ggtagaagga    180
tatacggttg atgtcaaaaa taaagaact tttctttcac catggatttc taatattcat     240
gaaaagaaag gattaaccaa atataaatca tctcctgaaa aatggagcac ggcttctgat    300
ccgtacagtg atttcaagcc gaattctgca gatatccatc acactggcgg ccgctcgagc    360
atgcatctag agggcccaat tcgccctata gtgagtcgta ttacaattca ctggccgtcg    420
ttttaca                                                              427

<210> SEQ ID NO 36
<211> LENGTH: 549
<212> TYPE: DNA
<213> ORGANISM: Artificial
<220> FEATURE:
<223> OTHER INFORMATION: Clone 7

<400> SEQUENCE: 36
caggaaacag ctatgaccat gattacgcca agcttggtac cgagctcgga tccactagta     60
acggccgcca gtgtgctgga attcggcttc aacgagaaaa tcctactgaa aaaggattgg    120
atcgttgtta ccgactggat tattaccaaa ataaaaaga gtgatttct agtgataact     180 tacaattgcc agaattaaaa caaaaatctt cgaactcaag aaaaacggat ggactgagag    240
cgatcaacta cgttccagac cgtgacaatg atggaatccc tgattcatta gaggtagaag    300
gatatacggt tgatgtcaaa ataaaagaa cttttctttc accatggatt tctaatattc    360
atgaaaagaa aggattaacc aaatataaat catctcctga aaatggagc acggcttctg    420 atccgtacag tgatttcaag ccgaattctg cagatatcca tcacactggc ggccgctcga    480
gcatgcatct agagggccca attcgcccta gtgagtcg tattacaatt cactggccgt    540
cgttttaca                                                            549

<210> SEQ ID NO 37
<211> LENGTH: 25
<212> TYPE: DNA
<213> ORGANISM: Artificial
<220> FEATURE:
<223> OTHER INFORMATION: MOD51U

<400> SEQUENCE: 37
tggtatgcgg aatccctgat tcatt                                           25

<210> SEQ ID NO 38
<211> LENGTH: 18
<212> TYPE: DNA
<213> ORGANISM: Artificial
<220> FEATURE:
<223> OTHER INFORMATION: PCR II FOR

<400> SEQUENCE: 38
caggaaacag ctatgacc                                                   18

<210> SEQ ID NO 39
<211> LENGTH: 262
<212> TYPE: DNA
<213> ORGANISM: Artificial
<220> FEATURE:
<223> OTHER INFORMATION: Fragment 10
```

```
<400> SEQUENCE: 39
caggaaacag ctatgaccat gattacgcca agcttggtac cgagctcgga tccactagta      60
acggccgcca gtgtgctgga attcggcttg aaatcactgt acggatcaga agccgtgctc     120 cattttcgg gagatgattt atatttggtt aatcctttct tttcatgaat attagaaatc      180
catggtgaaa gaaagttct tttatttttg acatcaaccg tatatccttc tacctctaat      240
gaatcaggga ttccgcatac ca                                              262

<210> SEQ ID NO 40
<211> LENGTH: 25
<212> TYPE: DNA
<213> ORGANISM: Artificial
<220> FEATURE:
<223> OTHER INFORMATION: MOD51L

<400> SEQUENCE: 40
gttgttgtcg aacgtagttg atcgc                                            25

<210> SEQ ID NO 41
<211> LENGTH: 18
<212> TYPE: DNA
<213> ORGANISM: Artificial
<220> FEATURE:
<223> OTHER INFORMATION: PCR II REV

<400> SEQUENCE: 41
tgtaaaacga cggccagt                                                    18

<210> SEQ ID NO 42
<211> LENGTH: 286
<212> TYPE: DNA
<213> ORGANISM: Artificial
<220> FEATURE:
<223> OTHER INFORMATION: Fragment 11

<400> SEQUENCE: 42
gttgttgtcg aacgtagttg atcgctctca gtccatccgt ttttcttgag ttcgaagatt      60
tttgttttaa ttctggcaat tgtaagttat cactagaaat cacttctttt ttattttggt     120
aataatccag tcggtaacaa cgatccaatc cttttcagt aggattttct cgttgaagcc      180
gaattctgca gatatccatc acactggcgg ccgctcgagc atgcatctag agggcccaat     240
tcgccctata gtgagcgtat tacaattcac tggccgtcgt tttaca                    286

<210> SEQ ID NO 43
<211> LENGTH: 21
<212> TYPE: DNA
<213> ORGANISM: Artificial
<220> FEATURE:
<223> OTHER INFORMATION: MOD52U

<400> SEQUENCE: 43
cgacaacaac tggtatgcgg a                                                21

<210> SEQ ID NO 44
<211> LENGTH: 18
<212> TYPE: DNA
<213> ORGANISM: Artificial
<220> FEATURE:
<223> OTHER INFORMATION: PCR II FOR

<400> SEQUENCE: 44
```
caggaaacag ctatgacc                                                           18

<210> SEQ ID NO 45
<211> LENGTH: 272
<212> TYPE: DNA
<213> ORGANISM: Artificial
<220> FEATURE:
<223> OTHER INFORMATION: Fragment 12

<400> SEQUENCE: 45
caggaaacag ctatgaccat gattacgcca agcttggtac cgagctcgga tccactagta      60
acggccgcca gtgtgctgga attcggcttg aaatcactgt acggatcaga agccgtgctc     120 cattttcgg gagatgattt atatttggtt aatcctttct tttcatgaat attagaaatc      180
catggtgaaa gaaaagttct tttattttg acatcaaccg tatatccttc tacctctaat      240
gaatcaggga ttccgcatac cagttgttgt cg                                    272

<210> SEQ ID NO 46
<211> LENGTH: 21
<212> TYPE: DNA
<213> ORGANISM: Artificial
<220> FEATURE:
<223> OTHER INFORMATION: MOD52L

<400> SEQUENCE: 46
tccgcatacc agttgttgtc g                                                21

<210> SEQ ID NO 47
<211> LENGTH: 18
<212> TYPE: DNA
<213> ORGANISM: Artificial
<220> FEATURE:
<223> OTHER INFORMATION: PCR II REV

<400> SEQUENCE: 47
tgtaaaacga cggccagt                                                    18

<210> SEQ ID NO 48
<211> LENGTH: 297
<212> TYPE: DNA
<213> ORGANISM: Artificial
<220> FEATURE:
<223> OTHER INFORMATION: Fragment 13

<400> SEQUENCE: 48
tccgcatacc agttgttgtc gaacgtagtt gatcgctctc agtccatccg ttttcttga       60 gttcgaagat ttttgtttta attctggcaa ttgtaagtta tcactagaaa tcacttcttt     120
tttattttgg taataatcca gtcggtaaca acgatccaat ccttttttcag taggattttc    180 tcgttgaagc cgaattctgc agatatccat cacactggcg gccgctcgag catgcatcta    240
gagggcccaa ttcgccctat agtgagcgta ttacaattca ctggccgtcg ttttaca        297

<210> SEQ ID NO 49
<211> LENGTH: 548
<212> TYPE: DNA
<213> ORGANISM: Artificial
<220> FEATURE:
<223> OTHER INFORMATION: IPC nucleic
      acid molecule

<400> SEQUENCE: 49
caggaaacag ctatgaccat gattacgcca agcttggtac cgagctcgga tccactagta      60

```
acggccgcca gtgtgctgga attcggcttg aaatcactgt acggatcaga agccgtgctc      120 cattttttcgg gagatgattt atatttggtt aatcctttct tttcatgaat attagaaatc     180
catggtgaaa gaaagttct tttatttttg acatcaaccg tatatccttc tacctctaat       240
gaatcaggga ttccgcatac cagttgttgt cgaacgtagt tgatcgctct cagtccatcc      300 gttttttcttg agttcgaaga ttttttgtttt aattctggca attgtaagtt atcactagaa    360
atcacttctt ttttattttg gtaataatcc agtcggtaac aacgatccaa tccttttttca    420 gtaggatttt ctcgttgaag ccgaattctg cagatatcca tcacactggc ggccgctcga     480
gcatgcatct agagggccca attcgcccta tagtgagcgt attacaattc actggccgtc     540
gttttaca                                                              548

<210> SEQ ID NO 50
<211> LENGTH: 25
<212> TYPE: DNA
<213> ORGANISM: Artificial
<220> FEATURE:
<223> OTHER INFORMATION: BAPA3U

<400> SEQUENCE: 50
ttcaagttgt actggaccga ttctc                                            25

<210> SEQ ID NO 51
<211> LENGTH: 21
<212> TYPE: DNA
<213> ORGANISM: Artificial
<220> FEATURE:
<223> OTHER INFORMATION: BAPA5L

<400> SEQUENCE: 51
tccatcattg tcacggtctg g                                                21

<210> SEQ ID NO 52
<211> LENGTH: 28
<212> TYPE: DNA
<213> ORGANISM: Artificial
<220> FEATURE:
<223> OTHER INFORMATION: BAPA3P2A

<400> SEQUENCE: 52
ccgtaggtcc agcacttgta cttcgctt                                         28

<210> SEQ ID NO 53
<211> LENGTH: 20
<212> TYPE: DNA
<213> ORGANISM: Artificial
<220> FEATURE:
<223> OTHER INFORMATION: BACAPBU2

<400> SEQUENCE: 53
gctgaccaat ctaagcctgc                                                  20

<210> SEQ ID NO 54
<211> LENGTH: 20
<212> TYPE: DNA
<213> ORGANISM: Artificial
<220> FEATURE:
<223> OTHER INFORMATION: BACAPBL2

<400> SEQUENCE: 54
ggcaaaacat ccctagcaaa                                                  20
```

```
<210> SEQ ID NO 55
<211> LENGTH: 27
<212> TYPE: DNA
<213> ORGANISM: Artificial
<220> FEATURE:
<223> OTHER INFORMATION: BACAPBP2

<400> SEQUENCE: 55
ttgtaattat gaattgccgc cctgacc                                              27

<210> SEQ ID NO 56
<211> LENGTH: 21
<212> TYPE: DNA
<213> ORGANISM: Artificial
<220> FEATURE:
<223> OTHER INFORMATION: BROMPF394

<400> SEQUENCE: 56
aacaaggcca agaccagcac c                                                    21

<210> SEQ ID NO 57
<211> LENGTH: 20
<212> TYPE: DNA
<213> ORGANISM: Artificial
<220> FEATURE:
<223> OTHER INFORMATION: BROMPR474

<400> SEQUENCE: 57
ctggaagttc cagccagcaa                                                      20

<210> SEQ ID NO 58
<211> LENGTH: 26
<212> TYPE: DNA
<213> ORGANISM: Artificial
<220> FEATURE:
<223> OTHER INFORMATION: BROMP25-420S

<400> SEQUENCE: 58
cagcatcaag cctgacgatt ggaagg                                               26

<210> SEQ ID NO 59
<211> LENGTH: 27
<212> TYPE: DNA
<213> ORGANISM: Artificial
<220> FEATURE:
<223> OTHER INFORMATION: CBOTA4U

<400> SEQUENCE: 59
gatataggct ttataggatt tcatcag                                              27

<210> SEQ ID NO 60
<211> LENGTH: 18
<212> TYPE: DNA
<213> ORGANISM: Artificial
<220> FEATURE:
<223> OTHER INFORMATION: CBOTA4L

<400> SEQUENCE: 60
cctttctccc catccatc                                                        18

<210> SEQ ID NO 61
<211> LENGTH: 26
<212> TYPE: DNA
<213> ORGANISM: Artificial
<220> FEATURE:
<223> OTHER INFORMATION: CBOTA4P2A
```

```
<400> SEQUENCE: 61
tcccatgagc aacccaaagt cctact                                          26

<210> SEQ ID NO 62
<211> LENGTH: 20
<212> TYPE: DNA
<213> ORGANISM: Artificial
<220> FEATURE:
<223> OTHER INFORMATION: YPPLA3U

<400> SEQUENCE: 62
ggtaccgtaa ttaacgctgg                                                 20

<210> SEQ ID NO 63
<211> LENGTH: 20
<212> TYPE: DNA
<213> ORGANISM: Artificial
<220> FEATURE:
<223> OTHER INFORMATION: YPPLA3L

<400> SEQUENCE: 63
gtctgagtac ctcctttgcc                                                 20

<210> SEQ ID NO 64
<211> LENGTH: 24
<212> TYPE: DNA
<213> ORGANISM: Artificial
<220> FEATURE:
<223> OTHER INFORMATION: YPPLAP3F

<400> SEQUENCE: 64
acctaatgcc aaagtctttg cgga                                            24

<210> SEQ ID NO 65
<211> LENGTH: 24
<212> TYPE: DNA
<213> ORGANISM: Artificial
<220> FEATURE:
<223> OTHER INFORMATION: BACAPB4U

<400> SEQUENCE: 65
cagataatgc atcgcttgct ttag                                            24

<210> SEQ ID NO 66
<211> LENGTH: 23
<212> TYPE: DNA
<213> ORGANISM: Artificial
<220> FEATURE:
<223> OTHER INFORMATION: BACAPB4L

<400> SEQUENCE: 66
ggatgagcat tcaacatacc acg                                             23

<210> SEQ ID NO 67
<211> LENGTH: 29
<212> TYPE: DNA
<213> ORGANISM: Artificial
<220> FEATURE:
<223> OTHER INFORMATION: BACAPBP1S

<400> SEQUENCE: 67
cagaggctct tgggattgat gaggaaaca                                       29

<210> SEQ ID NO 68
<211> LENGTH: 24
```

<212> TYPE: DNA
<213> ORGANISM: Artificial
<220> FEATURE:
<223> OTHER INFORMATION: BAVRRA3U

<400> SEQUENCE: 68
aaatgtatga atcaaacgaa acgc                                      24

<210> SEQ ID NO 69
<211> LENGTH: 20
<212> TYPE: DNA
<213> ORGANISM: Artificial
<220> FEATURE:
<223> OTHER INFORMATION: BAVRRA3L

<400> SEQUENCE: 69
cagggcttac agattgaacg                                           20

<210> SEQ ID NO 70
<211> LENGTH: 22
<212> TYPE: DNA
<213> ORGANISM: Artificial
<220> FEATURE:
<223> OTHER INFORMATION: BAVRRA3P1S

<400> SEQUENCE: 70
cggtgcagca actacagcag ca                                        22

<210> SEQ ID NO 71
<211> LENGTH: 25
<212> TYPE: DNA
<213> ORGANISM: Artificial
<220> FEATURE:
<223> OTHER INFORMATION: FTTULU1

<400> SEQUENCE: 71
cagcatacaa taataaccca caagg                                     25

<210> SEQ ID NO 72
<211> LENGTH: 25
<212> TYPE: DNA
<213> ORGANISM: Artificial
<220> FEATURE:
<223> OTHER INFORMATION: FTTULL1

<400> SEQUENCE: 72
tcagcatact tagtaattgg gaagc                                     25

<210> SEQ ID NO 73
<211> LENGTH: 26
<212> TYPE: DNA
<213> ORGANISM: Artificial
<220> FEATURE:
<223> OTHER INFORMATION: FTTULP1F

<400> SEQUENCE: 73
ttacaatggc aggctccaga aggttc                                    26

<210> SEQ ID NO 74
<211> LENGTH: 19
<212> TYPE: DNA
<213> ORGANISM: Artificial
<220> FEATURE:
<223> OTHER INFORMATION: YPPIMU1

<400> SEQUENCE: 74
agtggccttg cagaaaaaa                    19

<210> SEQ ID NO 75
<211> LENGTH: 21
<212> TYPE: DNA
<213> ORGANISM: Artificial
<220> FEATURE:
<223> OTHER INFORMATION: YPPIML1

<400> SEQUENCE: 75
gtaaactcgg tttgcttgaa g                 21

<210> SEQ ID NO 76
<211> LENGTH: 25
<212> TYPE: DNA
<213> ORGANISM: Artificial
<220> FEATURE:
<223> OTHER INFORMATION: YPPIMP1R

<400> SEQUENCE: 76
tgtctgtttc ccatagatgc catga             25

<210> SEQ ID NO 77
<211> LENGTH: 22
<212> TYPE: DNA
<213> ORGANISM: Artificial
<220> FEATURE:
<223> OTHER INFORMATION: OPSPF89

<400> SEQUENCE: 77
gatgatgcaa ctctatcatg ta                22

<210> SEQ ID NO 78
<211> LENGTH: 26
<212> TYPE: DNA
<213> ORGANISM: Artificial
<220> FEATURE:
<223> OTHER INFORMATION: OPSR219

<400> SEQUENCE: 78
gtataattat caaaatacaa gacgtc            26

<210> SEQ ID NO 79
<211> LENGTH: 18
<212> TYPE: DNA
<213> ORGANISM: Artificial
<220> FEATURE:
<223> OTHER INFORMATION: Op-p143S

<400> SEQUENCE: 79
agtgcttggt ataaggag                     18

<210> SEQ ID NO 80
<211> LENGTH: 24
<212> TYPE: DNA
<213> ORGANISM: Artificial
<220> FEATURE:
<223> OTHER INFORMATION: FOPAF708

<400> SEQUENCE: 80
ctggtttaac atggttcttt ggtg              24

<210> SEQ ID NO 81
<211> LENGTH: 27
<212> TYPE: DNA
<213> ORGANISM: Artificial

```
<220> FEATURE:
<223> OTHER INFORMATION: FOPAR846

<400> SEQUENCE: 81
ccagcaggta aaacatactt agactca                                    27

<210> SEQ ID NO 82
<211> LENGTH: 28
<212> TYPE: DNA
<213> ORGANISM: Artificial
<220> FEATURE:
<223> OTHER INFORMATION: FtFOPA765S

<400> SEQUENCE: 82
tccaggataa tggtgcgact acagctgc                                   28

<210> SEQ ID NO 83
<211> LENGTH: 20
<212> TYPE: DNA
<213> ORGANISM: Artificial
<220> FEATURE:
<223> OTHER INFORMATION: J7R3U

<400> SEQUENCE: 83
catcattggc ggttgattta                                            20

<210> SEQ ID NO 84
<211> LENGTH: 21
<212> TYPE: DNA
<213> ORGANISM: Artificial
<220> FEATURE:
<223> OTHER INFORMATION: J7R3L

<400> SEQUENCE: 84
tcatctggag aatccacaac a                                          21

<210> SEQ ID NO 85
<211> LENGTH: 26
<212> TYPE: DNA
<213> ORGANISM: Artificial
<220> FEATURE:
<223> OTHER INFORMATION: VARJ7R3p

<400> SEQUENCE: 85
caagacgtcg ggaccaatta ctaata                                     26

<210> SEQ ID NO 86
<211> LENGTH: 19
<212> TYPE: DNA
<213> ORGANISM: Artificial
<220> FEATURE:
<223> OTHER INFORMATION: BPISO2F1

<400> SEQUENCE: 86
ctcgaggtgg agaatgccc                                             19

<210> SEQ ID NO 87
<211> LENGTH: 21
<212> TYPE: DNA
<213> ORGANISM: Artificial
<220> FEATURE:
<223> OTHER INFORMATION: BPISO2R1

<400> SEQUENCE: 87
cgctcggaga tgttgacctt c                                          21
```

<210> SEQ ID NO 88
<211> LENGTH: 24
<212> TYPE: DNA
<213> ORGANISM: Artificial
<220> FEATURE:
<223> OTHER INFORMATION: BMISO2PF3

<400> SEQUENCE: 88
tggccgaagc aatgctcgat atgg                                          24

<210> SEQ ID NO 89
<211> LENGTH: 153
<212> TYPE: DNA
<213> ORGANISM: Artificial
<220> FEATURE:
<223> OTHER INFORMATION: IPC amplicon

<400> SEQUENCE: 89
tccgcatacc agttgttgtc gaacgtagtt gatcgctctc agtccatccg tttttcttga    60
gttcgaagat ttttgtttta attctggcaa ttgtaagtta tcactagaaa tcacttcttt   120
tttattttgg taataatcca gtcggtaaca acg                                153

<210> SEQ ID NO 90
<211> LENGTH: 453
<212> TYPE: RNA
<213> ORGANISM: Artificial
<220> FEATURE:
<223> OTHER INFORMATION: IPC RNA

<400> SEQUENCE: 90
gggcgaauug ggcccucuag augcaugcuc gagcggccgc cagugugaug gauaucugca    60
gaauucggcu ucaacgagaa auccuacug aaaaaggauu ggaucguugu uaccgacugg   120
auuauuacca aauaaaaaa gaagugauuu cuagugauaa cuuacaauug ccagaauuaa   180
aacaaaaauc uucgaacuca agaaaaacgg auggacugag agcgaucaac uacguucgac   240
aacaacuggu augcggaauc ccugauucau uagaguaga aggauauacg guugauguca   300 aaauaaaag aacuuuucuu ucaccaugga uuucuaauau ucaugaaaag aaaggauuaa   360
ccaaauauaa aucaucuccc gaaaauggag cacggcuucu gauccguaca gugauuucaa   420
gccgaauucc agcacacugg cggccguuac uag                                453

<210> SEQ ID NO 91
<211> LENGTH: 153
<212> TYPE: RNA
<213> ORGANISM: Artificial
<220> FEATURE:
<223> OTHER INFORMATION: RT-IPC amplicon

<400> SEQUENCE: 91
cguuguuacc gacuggauua uuaccaaaau aaaaagaag ugauuucuag ugauaacuua    60
caauugccag aauuaaaaca aaaaucuucg aacucaagaa aaacggaugg acugagagcg   120
aucaacuacg uucgacaaca acugguaugc gga                                153

INTERNAL POSITIVE CONTROL FOR PROBE-BASED NUCLEIC ACID MOLECULE ASSAYS AND METHODS OF MAKING AND USING THEREOF

CROSS REFERENCE TO RELATED APPLICATIONS

This application is a continuation-in-part of U.S. patent application Ser. No. 10/376,323, filed 3 Mar. 2003, allowed, which claims the benefit of U.S. Provisional Patent Application No. 60/361,455, filed 4 Mar. 2002, abandoned, which names Laurie J. Hartman and David A. Norwood, Jr. as co-inventors and are herein incorporated by reference in their entirety.

ACKNOWLEDGMENT OF GOVERNMENT SUPPORT

Employees of the United States Army made this invention. The government has rights in the invention.

BACKGROUND OF THE INVENTION

1. Field of the Invention

The present invention generally relates to probes comprising a reporter molecule and a quencher molecule for use in nucleic acid assays. In particular, the present invention relates to a universal internal positive control that may be used in reverse transcriptase polymerase chain reaction (RT-PCR) based assays.

2. Description of the Related Art

Reporter molecule and quencher molecule pairs have been incorporated onto oligonucleotide probes in order to monitor, detect, or measure biological events associated with the reporter molecule and quencher molecule being separated or brought within a minimum quenching distance of each other. For example, probes have been developed where the intensity of the reporter molecule fluorescence increases due to the separation of the reporter molecule from the quencher molecule. Probes have also been developed which lose their fluorescence because the quencher molecule is brought into proximity with the reporter molecule. Reporter molecule and quencher molecule pair probes have been used to monitor hybridization assays and nucleic acid amplification reactions, such as polymerase chain reactions (PCR), by monitoring either the appearance or disappearance of the signal generated by the reporter molecule. See WO 90/03446; European Patent Application No. 0 601 889 A2; Mergney, et al., (1994) Nucleic Acids Research 22(6): 920–928; and Amheim and Erlich, (1992) Ann. Rev. Biochem. 61:131–156.

Various real time PCR amplification product assays are known in the art. See e.g. Holland et al. (1991) PNAS 88:7276–7280; and U.S. Pat. No. 5,210,015. One assay uses a probe having a fluorescence reporter molecule and quencher molecule pair that is cleaved apart during amplification thereby resulting in a detectable fluorescent molecule in a concentration that is proportional to the amount of double-stranded DNA. These assays are known as Taq-Man® based assays. TaqMan® based assays use an oligonucleotide probe having a reporter molecule and quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule.

During strand extension by a DNA polymerase, the probe anneals to the template where it is digested by the 5'→3' exonuclease activity of the polymerase. As a result of the probe being digested, the reporter molecule is effectively separated from the quencher molecule such that the quencher molecule is no longer close enough to the reporter molecule to quench the fluorescence of the reporter molecule. Thus, as more and more probes are digested during amplification, the number of reporter molecules in solution increases, thereby resulting in an increasing number of unquenched reporter molecules which produce a stronger and stronger fluorescent signal.

TaqMan® based assays require internal positive control reagents to help distinguish between samples that are identified as negative because the sample lacks the target sequence and samples that are identified as negative because the presence of a PCR inhibitor. A TaqMan® Exogenous Internal Positive Control kit is commercially available from Applied Biosystems (Foster City, Calif.) to distinguish true target negatives from PCR inhibition. The TaqMan® Exogenous Internal Positive Control kit distinguishes two types of negative results. A negative call for the target sequence and a positive call for the internal positive control (IPC) indicates that no target sequence is present and a negative call for the target sequence and a negative call for the IPC suggests PCR inhibition.

Unfortunately, the TaqMan® Exogenous Internal Positive Control kits allow little flexibility as the kits are made with only one fluorescent dye, VIC™ (Applied Biosystems, Foster City, Calif.), which cannot be used on all TaqMan® chemistry based instruments and the primers and probe in the kit are mixed together by the manufacturer and therefore cannot be completely optimized for use with any PCR amplification product assay.

Thus, a need exists for an internal positive control that may be used with a variety of PCR amplification product assays.

SUMMARY OF THE INVENTION

The present invention generally relates to a nucleic acid molecule that may be used as an internal positive control in probe-based nucleic acid assays.

In some embodiments, the present invention relates to an isolated nucleic acid molecule comprising the sequence set forth in SEQ ID NO:49. In some embodiments, the nucleic acid molecule consists essentially of the sequence set forth in SEQ ID NO:49. In some embodiments, the nucleic acid molecule consists of the sequence set forth in SEQ ID NO:49.

In some embodiments, the present invention provides an isolated nucleic acid molecule comprising at least 80 consecutive bases of SEQ ID NO:89 or its complement. In some embodiments, the isolated nucleic acid molecule comprises SEQ ID NO:89 or its complement. In some embodiments, the isolated nucleic acid molecule comprises SEQ ID NO:49 or its complement, SEQ ID NO:90. In some embodiments, the isolated nucleic acid molecule consists essentially of SEQ ID NO:89 or its complement. In some embodiments, the isolated nucleic acid molecule consists essentially of SEQ ID NO:49 or its complement, SEQ ID NO:90. In some embodiments, the isolated nucleic acid molecule consists of SEQ ID NO:89 or its complement. In some embodiments, the isolated nucleic acid molecule consists of SEQ ID NO:49 or its complement, SEQ ID NO:90.

In some embodiments, the present invention provides an isolated nucleic acid molecule that has a sequence identity of at least about 70% over the 548 bp region of SEQ ID NO:49. In preferred embodiments, the sequence identity is at least about 80%, preferably at least about 90%, more preferably at least about 95%.

In some embodiments, the present invention provides a probe comprising an isolated nucleic acid molecule of the present invention and a label.

In some embodiments, the present invention provides a probe comprising an isolated nucleic acid molecule of the present invention, a reporter molecule, and a quencher molecule. In preferred embodiments, the reporter molecule produces a signal upon the separation of the reporter molecule and the quencher molecule. In preferred embodiments, the quencher molecule is capable of quenching the signal of the reporter molecule. In some embodiments, the reporter molecule is a fluorophore such as FAM, ROX, Texas Red, TET, TAMRA, JOE, HEX, CAL Red, and VIC, preferably the fluorophore is FAM, ROX, or Texas Red. In some embodiments, the probe is capable of being cleaved by a protein thereby separating the reporter molecule from the quencher molecule. In preferred embodiments, the protein is Taq polymerase.

In some embodiments, the present invention provides an assay which comprises using a probe of the present invention. In preferred embodiments, the assay is a nucleic acid hybridization assay such as a TaqMan® based assay. In some embodiments, the assay further comprises conducting PCR amplification. The assay may further comprise detecting the presence or measuring the amount of the probe and detecting the presence or measuring the amount of a target nucleic acid molecule. In preferred embodiments of the present invention, the absence of the target nucleic acid molecule and the absence of the probe indicate a false negative result for the target nucleic acid molecule and the absence of the target nucleic acid molecule and the presence of the probe indicate a true negative result for the target nucleic acid molecule.

In some embodiments, the present invention provides a kit for a probe-based nucleic acid assay comprising an isolated nucleic acid molecule of the present invention packaged with instructions for use. In preferred embodiments, the isolated nucleic acid molecule contains a label such as a reporter molecule and a quencher molecule. In some embodiments, the probe-based nucleic acid assay is for the detection of an organism such as one belonging to *Bacillus, Mycobacterium, Francisella, Brucella, Clostridium, Yersinia, Variola, Orthopox*, or *Burkholderia*. The kit of the present invention may further include reagents or components for detecting the presence of a nucleic acid molecule belonging to the organism.

In some embodiments, the present invention also provides a method of making an internal positive control nucleic acid molecule for a probe-based nucleic acid molecule assay which comprises creating a first DNA fragment and a second DNA fragment from a template DNA and first set of primers and a second set of primers; creating a third DNA fragment and a fourth DNA fragment from the first DNA fragment and the second DNA fragment with a third set of primers and a second set of primers; hybridizing the third DNA fragment and the fourth DNA fragment to obtain a first hybridized DNA; using a fifth primer set to create a fifth DNA fragment from the first hybridized DNA; using a sixth primer set and a seventh primer set to create a sixth DNA fragment and a seventh DNA fragment from the fifth DNA fragment; creating a eighth DNA fragment and a ninth DNA fragment from the sixth DNA fragment and the seventh DNA fragment using a eighth primer set and a ninth primer set; hybridizing the eighth DNA fragment and the ninth DNA fragment to obtain a second hybridized DNA; creating a tenth DNA fragment and an eleventh DNA fragment from the second hybridized DNA using a tenth set of primers and an eleventh set of primers; creating a twelfth DNA fragment and a thirteenth DNA fragment from the tenth DNA fragment and the eleventh DNA fragment using a twelfth set of primers and a thirteenth set of primers; hybridizing the twelfth DNA fragment and the thirteenth DNA fragment to obtain the internal positive control nucleic acid molecule. In some preferred embodiments, the method of making an internal positive control nucleic acid molecule for a probe-based nucleic acid molecule assay, wherein the internal positive control nucleic acid molecule contains a sequence that has a sequence identity of at least about 70% over the 548 bp region of SEQ ID NO:49. In preferred embodiments, the sequence identity is at least about 80%, preferably at least about 90%, more preferably at least about 95%.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 is a schematic showing an example of a TaqMan® based assay.

FIG. 2 schematically shows the site-directed mutagenesis process used to generate the IPC nucleic acid molecule of the present invention.

FIG. 3 shows the gel of Example 4B.

FIG. 4 shows an agarose gel electrophoresis of denatured in vitro transcribed IPC RNA.

FIG. 5 shows DMSO is completely inhibitory at 25% and was partially inhibitory at 6.25%.

FIG. 6 shows guanidine hydrochloride was completely inhibitory at 200 mM and 100 mM.

FIG. 7 shows guanidine thiocyanate was completely inhibitory at 100 mM and 50 mM.

FIG. 8 shows heparin was completely inhibitory at 0.00125 Units.

FIG. 9 shows SDS was completely inhibitory at 0.02% and 0.01%.

FIG. 10 shows glycerol was completely inhibitory at 25%, 12.5%, and 6.25%.

FIG. 11 shows formamide was completely inhibitory at 25%, 12.5%, 6.25%, and 3.125%.

FIG. 12 shows EDTA was completely inhibitory at 5 mM and 2.5 mM.

DETAILED DESCRIPTION OF THE INVENTION

The present invention provides an internal positive control (IPC) for use in nucleic acid hybridization assays, preferably probe-based nucleic acid assays such as TaqMan® based assays. An example of a TaqMan® based assay is schematically shown in FIG. 1. In particular, the present invention provides an oligonucleotide (IPC oligonucleotide) having a reporter molecule and a quencher molecule. The IPC oligonucleotide specifically anneals between the forward and reverse primers of a target sequence. The IPC oligonucleotide is cleaved by the 5' nuclease activity of Taq polymerase during PCR amplification and the reporter molecule is then separated from the quencher molecule to generate a sequence specific signal. With each amplification cycle, additional reporter molecules are separated from the quencher molecules. The intensity of a signal, such as fluorescence, may be monitored before, during, or after PCR amplification or a combination thereof.

The IPC nucleic acid molecule of the present invention may be used to distinguish a true negative result from a false negative result. As used herein, a "true negative" result correctly indicates that a sample lacks a target nucleic acid sequence. A "false negative" result incorrectly indicates the absence of a target nucleic acid sequence which may result from PCR inhibitors present in the sample or technical error.

The IPC nucleic acid molecule of the present invention may be used as a universal internal control as it comprises unique primer and probe sites and does not exhibit homology with any known nucleic acid sequences that may interfere with this assay, i.e. does not anneal with known nucleic acid sequences during conventional PCR techniques.

The IPC nucleic acid molecule of the present invention provides greater flexibility over commercially available IPCs as a variety of reporter molecule and quencher molecule pairs may be used and since the primers, probes, and IPC nucleic acid molecule sequences are independent, various concentrations of each may be used.

As described herein, the 153 base pair (bp) product from a *Bacillus anthracis* Protective Antigen (PA) PCR assay developed by the Diagnostic Systems Division (DSD) at the United States Army Medical Research Institute of Infectious Diseases (USAMRIID) was used (publication in progress). The 153 bp sequence is:

```
5' TTCAAGTTGT ACTGGACCGA TTCTCAAAAT    (SEQ ID NO:1)

AAAAAAGAAG TGATTTCTAG TGATAACTTA

CAATTGCCAG AATTAAAACA AAAATCTTCG

AACTCAAGAA AAAAGCGAAG TACAAGTGCT

GGACCTACGG TTCCAGACCG TGACAATGAT

GGA 3'.
```

The probe and both primer sites were mutated to predetermined sequences as follows:

```
Upper Primer: IPC3L
5' CGT TGT TAC CGA CTG GAT TAT TAC    (SEQ ID NO:2)
C 3';

Lower Primer: IPC5U
5' TCC GCA TAC CAG TTG TTG TCG 3';    (SEQ ID NO:3)
and

Probe: IPCP35F
5' CGT AGT TGA TCG CTC TCA GTC CAT    (SEQ ID NO:4)
CCG T 3'.
```

The original sequences were randomized and the random sequences were checked with a nucleotide BLAST search to confirm their uniqueness. The original sequences of the PA assay are as follows:

```
Upper Primer: BAPA3U
5' TTC AAG TTG TAC TGG ACC GAT TCT    (SEQ ID NO:5)
C 3';

Lower Primer: BAPA5L
5' TCC ATC ATT GTC ACG GTC TGG 3';    (SEQ ID NO:6)
and

Probe: BAPA3P2A
5' CCG TAG GTC CAG CAC TTG TAC TTC    (SEQ ID NO:7)
GCT T 3'.
```

The probe site was mutated first, followed by the upper primer site and then finally the lower primer site. As disclosed in Example 1, the mutations were conducted with PCR-based site directed mutagenesis methods known in the art. See Courtney, B. C., et al. (1999) Analytical Biochemistry 270:249–256. The methods were the same for all three sites, the only differences were the mutagenic oligonucleotide sequences.

Generally, mutations of each site were performed in three stages comprising five steps. For the initial probe mutation, genomic *Bacillus anthracis* DNA was used, and for the subsequent primer mutations, the plasmid DNA from the clone of the previous mutation was used. Mutagenic oligonucleotides were used to introduce the desired mutations. For round 1, these oligos contained ½ the sequence of *B. anthracis* genomic DNA and ½ the sequence of the desired mutation. These mutagenic oligos were paired up with an oligo outside of the final 153 bp PA product. When amplified with PCR, the result was two products each containing half of the final desired mutation sequence. For round 2, these mutagenic oligos consisted of ½ the new sequence that was introduced in round 1 and ½ the sequence of the rest of the desired mutation. The two products from round 1 were used as templates. Again, these mutagenic oligos were paired up with an oligo outside of the final 153 bp PA product. When amplified with PCR, the result was two products each containing all of the final desired mutation sequence. Finally in round 3, the two products from round 2 were used as primers on each other and ligated together, in addition the two oligos outside of the 153 bp product were used to further amplify it and increase the copy number of the final product. This final product was ligated into the pCR2.1 vector (Invitrogen Corporation, Carlsbad, Calif.) and transformed into competent INVαF' *E. coli* (Invitrogen Corporation, Carlsbad, Calif.).

For round 1 of the probe mutation, the template DNA used was 1 ng of Ames genomic DNA (USAMRIID, Ft. Detrick, Md.), and the primers were:

```
BANPAIS1
5' GTA ACA ATG TGG GTA GAT GAC C 3'    (SEQ ID NO:8)

PA35PC1L
5' TCT CAG TCC ATC CGT TTT TCT TGA    (SEQ ID NO:9)
GTT C 3'
```

The product, Fragment 1, was a 252 bp product as follows:

5' GTAACAATGTGGGTAGATGACCAAGAAGTGATTAATAAAGCTTCTAATTCTAACAAAATCAGATTAGAAAAAGGAAGATTATA    (SEQ ID NO:10)

TCAAATAAAAATTCAATATCAACGAGAAAATCCTACTGAAAAAGGATTGGATTTCAAGTTGTACTGGACCGATTCTCAAAATAAAA

AAGAAGTGATTTCTAGTGATAACTTACAATTGCCAGAATTAAAACAAAAATCTTCGAACTCAAGAAAAACGGATGGACTGAGA 3'.

Also for round 1 of the probe mutation, the template DNA used was 1 ng of Ames genomic DNA (USAMRIID, Ft. Detrick, Md.), and the primers were:

```
BANPAIA1
5' CTT ATC AAT CCG TCC TGT AAC C 3'  (SEQ ID NO:11)

PA35PC1U
5' GCG ATC AAC TAC GTT CCA GAC CGT   (SEQ ID NO:12)
G 3'
```

The product, Fragment 2, was a 225 bp product as follows:

```
5' GCGATCAACTACGTTCCAGACCGTGACAATGATGGAATCCCTGATTCATTAGAGGTAGAAGGATATACGGTTGATGTCAAAA   (SEQ ID NO:13)

ATAAAAGAACTTTTCTTTCACCATGGATTTCTAATATTCATGAAAAGAAAGGATTAACCAAATATAAATCATCTCCTGAAAAATG

GAGCACGGCTTCTGATCCGTACAGTGATTTCGAAAAGGTTACAGGACGGATTGATAAG 3'.
```

Both Fragment 1 and Fragment 2 were purified with the QIAquick PCR Purification Kit (Qiagen, Valencia, Calif.).

For round 2 of the probe mutation, the template DNA used was Fragment 1, the 252 bp product from BANPAIS1/PA35PC1L, and the primers used were:

```
BANPAIS1
5' GTA ACA ATG TGG GTA GAT GAC C 3'  (SEQ ID NO:14)

PA35PC2L
5' CGT AGT TGA TCG CTC TCA GTC CAT   (SEQ ID NO:15)
CCG T 3'
```

The product, Fragment 3, was a 265 bp product as follows:

```
5' GTAACAATGTGGGTAGATGACCAAGAAGTGATTAATAAAGCTTCTAATTCTAACAAAATCAGATTAGAAAAAGGAAGATTAT   (SEQ ID NO:16)

ATCAAATAAAAATTCAATATCAACGAGAAAATCCTACTGAAAAAGGATTGGATTTCAAGTTGTACTGGACCGATTCTCAAAATAA

AAAAGAAGTGATTTCTAGTGATAACTTACAATTGCCAGAATTAAAACAAAAATCTTCGAACTCAAGAAAAACGGATGGACTGAGA

GCGATCAACTACG 3'.
```

Also for round 2 of the probe mutation, the template DNA used was Fragment 2, the 225 bp product from BANPAIA1/PA35PC1U, and the primers used were:

```
BANPAIA1
5' CTT ATC AAT CCG TCC TGT AAC C 3'  (SEQ ID NO:17)
```

-continued

```
PA35PC1U
5' ACG GAT GGA CTG AGA GCG ATC AAC   (SEQ ID NO:18)
TAC G 3'
```

The product, Fragment 4, was a 240 bp product as follows:

5' ACGGATGGACTGAGAGCGATCAACTACGTTCCAGACCGTGACAATGATGGAATCCCTGATTCATTAGAGGTAGAAGGATATA (SEQ ID NO:19)

CGGTTGATGTCAAAAATAAAAGAACTTTTCTTTCACCATGGATTTCTAATATTCATGAAAAGAAAGGATTAACCAAATATAAATC

ATCTCCTGAAAAATGGAGCACGGCTTCTGATCCGTACAGTGATTTCGAAAAGGTTACAGGACGGATTGATAAG 3'

Both Fragment 3 and Fragment 4 were purified with the QIAquick PCR Purification Kit (Qiagen, Valencia, Calif.).

For round 3, Fragment 3 (265 bp product from BANPAIS1/PA35PC2L) was hybridized with Fragment 4 (240 bp product from BANPAIA1/PA35PC2U). An additional 1 μM each of BANPAIS1 and BANPAIA1 primers were added to create more product. A new primer set that was inside BANPAIS1/BANPAIA1, but still outside BAPA3U/BAPA5L was developed. The primers set is as follows:

BANPABIS1
5' CAA CGA GAA AAT CCT ACT GAA AAA (SEQ ID NO:20)

-continued

G 3'

BANPABIA1
5' GAA ATC ACT GTA CGG ATC AGA AGC (SEQ ID NO:21)

3'

Round 3 was repeated with the addition of the new primer set. The product, Fragment 5, was 348 bp product and is as follows:

5' CAACGAGAAAATCCTACTGAAAAAGGATTGGATTTCAAGTTGTACTGGACCGATTCTCAAAATAAAAAAGAAGTGATTTCTA (SEQ ID NO:22)

GTGATAACTTACAATTGCCAGAATTAAAACAAAAATCTTCGAACTCAAGAAAAACGGATGGACTGAGAGCGATCAACTACGTTCC

AGACCGTGACAATGATGGAATCCCTGATTCATTAGAGGTAGAAGGATATACGGTTGATGTCAAAAATAAAAGAACTTTTCTTTCA

CCATGGATTTCTAATATTCATGAAAAGAAAGGATTAACCAAATATAAATCATCTCCTGAAAAATGGAGCACGGCTTCTGATCCGT

ACAGTGATTTC 3'.

Fragment 5 was gel purified with the QIAquick Gel Extraction Kit and cloned using the Original TA Cloning Kit (Invitrogen Corporation, Carlsbad, Calif.). All of the clones were sequenced with both forward and reverse primers in duplicate. Clone 11 was chosen because it had the exact mutated sequence that we were trying to achieve and the rest of the sequence remained unaltered. The Qiagen Plasmid Mini Purification Kit (Qiagen, Carlsbad, Calif.) was used to purify the plasmid DNA for further mutations.

For round 1 of the upper primer mutation, the template DNA used was 1 ng of purified plasma DNA from Clone 11 having the following sequence:

5' GAAACAGCTATGACCATGATTACGCCAAGCTTGGTACCGAGCTCGGATCCACTAGTAACGGCCGCCAGTGTGCTGGAATTCG (SEQ ID NO:23)

GCTTCAACGAGAAAATCCTACTGAAAAAGGATTGGATTTCAAGTTGTACTGGACCGATTCTCAAAATAAAAAAGAAGTGATTTCT

AGTGATAACTTACAATTGCCAGAATTAAAACAAAAATCTTCGAACTCAAGAAAAACGGATGGACTGAGAGCGATCAACTACGTTC

CAGACCGTGACAATGATGGAATCCCTGATTCATTAGAGGTAGAAGGATATACGGTTGATGTCAAAAATAAAAGAACTTTTCTTTC

ACCATGGATTTCTAATATTCATGAAAAGAAAGGATTAACCAAATATAAATCATCTCCCGAAAAATGGAGCACGGCTTCTGATCCG

TACAGTGATTTCAAGCCGAATTCTGCAGATATCCATCACACTGGCGGCCGCTCGAGCATGCATCTAGAGGGCCCAATTCGCCCTA

TAGTGAGTCGTATT 3'.

The primers used were as follows:

```
MOD31L
5' TCG GTA ACA ACG ATC CAA TCC TTT     (SEQ ID NO:24)
T 3'.

PCR II FOR
5' CAG GAA ACA GCT ATG ACC 3'.         (SEQ ID NO:25)
```

The product, Fragment 6, was a 134 bp product as follows:

5' CAGGAAACAGCTATGACCATGATTACGCCAAGCTTGGTACCGAGCTCGGATCCACTAGTAACGGCCGC     (SEQ ID NO:26)

CAGTGTGCTGGAATTCGGCTTCAACGAGAAAATCCTACTGAAAAAGGATTGGATCGTTGTTACCGA 3'.

Also for round 1 of the upper primer mutation, the template DNA used was 1 ng of purified plasma DNA from Clone 11 and the primers used were as follows:

```
MOD31U
5' CTG GAT TAT TAC CAA AAT AAA AAA     (SEQ ID NO:27)
G 3'.

PCR II REV
5' TGT AAA ACG ACG GCC AGT 3'.         (SEQ ID NO:28)
```

The product, Fragment 7, was a 415 bp product as follows:

5' CTGGATTATTACCAAAATAAAAAAGAAGTGATTTCTAGTGATAACTTACAATTGCCAGAATTAAAACAAAAATCTTCGAACT     (SEQ ID NO:29)

CAAGAAAAACGGATGGACTGAGAGCGATCAACTACGTTCCAGACCGTGACAATGATGGAATCCCTGATTCATTAGAGGTAGAAGG

ATATACGGTTGATGTCAAAAATAAAAGAACTTTTCTTTCACCATGGATTTCTAATATTCATGAAAAGAAAGGATTAACCAAATAT

AAATCATCTCCTGAAAAATGGAGCACGGCTTCTGATCCGTACAGTGATTTCAAGCCGAATTCTGCAGATATCCATCACACTGGCG

GCCGCTCGAGCATGCATCTAGAGGGCCCAATTCGCCCTATAGTGAGTCGTATTACAATTCACTGGCCGTCGTTTTACA 3'.

Fragment 6 and Fragment 7 were purified with the QIAquick PCR Purification Kit (Qiagen, Valencia, Calif.).

For round 2 of the upper primer mutation, the template used was Fragment 6, the 134 bp product from MOD31L/PCR II FOR, and the primers used were as follows:

```
MOD32L
5' GGT AAT AAT CCA GTC GGT AAC AAC     (SEQ ID NO:30)
G 3'.

PCR II FOR
5' CAG GAA ACA GCT ATG ACC 3'.         (SEQ ID NO:31)
```

The product, Fragment 8, is a 147 bp product as follows:

5' CAGGAAACAGCTATGACCATGATTACGCCAAGCTTGGTACCGAGCTCGGATCCACTAGTAACGGCCGCCAGTGT     (SEQ ID NO:32)

GCTGGAATTCGGCTTCAACGAGAAAATCCTACTGAAAAAGGATTGGATCGTTGTTACCGACTGGATTATTACC 3'.

Also for round 2 of the upper primer mutation, the template used was Fragment 7, the 415 bp product from MOD31U/PCR II REV, and the primers used were as follows:

```
MOD32U
5' CGT TGT TAC CGA CTG GAT TAT TAC    (SEQ ID NO:33)
C 3'.

PCR II REV
5' TGT AAA ACG ACG GCC AGT 3'.        (SEQ ID NO:34)
```

The product, Fragment 9, was a 427 bp product as follows:

```
MOD51U
5' TGG TAT GCG GAA TCC CTG ATT CAT    (SEQ ID NO:37)
T 3'.

PCR II FOR
5' CAG GAA ACA GCT ATG ACC 3'         (SEQ ID NO:38)
```

The product, Fragment 10, was a 262 bp product as follows:

```
5' CGTTGTTACCGACTGGATTATTACCAAAATAAAAAAGAAGTGATTTCTAGTGATAACTTACAATTGCCAGAATTAAAACAAA   (SEQ ID NO:35)
AATCTTCGAACTCAAGAAAAACGGATGGACTGAGAGCGATCAACTACGTTCCAGACCGTGACAATGATGGAATCCCTGATTCATT
AGAGGTAGAAGGATATACGGTTGATGTCAAAAATAAAAGAACTTTTCTTTCACCATGGATTTCTAATATTCATGAAAAGAAAGGA
TTAACCAAATATAAATCATCTCCTGAAAAATGGAGCACGGCTTCTGATCCGTACAGTGATTTCAAGCCGAATTCTGCAGATATCC
ATCACACTGGCGGCCGCTCGAGCATGCATCTAGAGGGCCCAATTCGCCCTATAGTGAGTCGTATTACAATTCACTGGCCGTCGTT
TTACA 3'.
```

Fragment 8 and Fragment 9 were purified with the QIAquick Gel Extraction Kit (Qiagen, Valencia, Calif.).

For round 3, Fragment 8 and Fragment 9 were hybridized. Additional PCR II FOR and PCR II REV primers were added. The product was 549 bp as follows:

```
5' CAGGAAACAGCTATGACCATGATTACGCCAAGCTTGGTACCGAGCTCGGATCCACTAGTAACGGCCGCCAGTGTGCTGGAAT    (SEQ ID NO:36)
TCGGCTTCAACGAGAAAATCCTACTGAAAAAGGATTGGATCGTTGTTACCGACTGGATTATTACCAAAATAAAAAAGAAGTGATT
TCTAGTGATAACTTACAATTGCCAGAATTAAAACAAAAATCTTCGAACTCAAGAAAAACGGATGGACTGAGAGCGATCAACTACG
TTCCAGACCGTGACAATGATGGAATCCCTGATTCATTAGAGGTAGAAGGATATACGGTTGATGTCAAAAATAAAAGAACTTTTCT
TTCACCATGGATTTCTAATATTCATGAAAAGAAAGGATTAACCAAATATAAATCATCTCCTGAAAAATGGAGCACGGCTTCTGAT
CCGTACAGTGATTTCAAGCCGAATTCTGCAGATATCCATCACACTGGCGGCCGCTCGAGCATGCATCTAGAGGGCCCAATTCGCC
CTATAGTGAGTCGTATTACAATTCACTGGCCGTCGTTTTACA 3'.
```

```
5' CAGGAAACAGCTATGACCATGATTACGCCAAGCTTGGTACCGAGCTCGGATCCACTAGTAACGGCCGCCAGTGTGCTGGAAT    (SEQ ID NO:39)
TCGGCTTGAAATCACTGTACGGATCAGAAGCCGTGCTCCATTTTTCGGGAGATGATTTATATTTGGTTAATCCTTTCTTTTCATG
AATATTAGAAATCCATGGTGAAAGAAAAGTTCTTTTATTTTTGACATCAACCGTATATCCTTCTACCTCTAATGAATCAGGGATT
CCGCATACCA 3'.
```

The product was gel purified with the QIAquick Gel Extraction Kit and cloned using the Original TA Cloning Kit (Invitrogen Corp., Carlsbad, Calif.). All of the clones were sequenced with both forward and reverse primers in duplicate. Clone 7 was selected because it had the exact mutation sequence that we were trying to achieve, and the rest of the sequence remained unaltered. The plasmid DNA was purified using a Qiagen Plasmid Mini Purification Kit (Qiagen, Carlsbad, Calif.).

For round 1 of the lower primer mutation, the template DNA used was 1 ng of the purified plasmid DNA from clone 7. The primers used were as follows:

Also for round 1 of the lower primer mutation, the template used was 1 ng of the purified plasmid DNA from clone 7, and the primers used were as follows:

```
MOD51L
5' GTT GTT GTC GAA CGT AGT TGA TCG    (SEQ ID NO:40)
C 3'

PCR II REV
5' TGT AAA ACG ACG GCC AGT 3'         (SEQ ID NO:41)
```

The product, Fragment 11, was a 286 bp product as follows:

5' GTTGTTGTCGAACGTAGTTGATCGCTCTCAGTCCATCCGTTTTTCTTGAGTTCGAAGATTTTTGTTTTAATTCTGGCAATTG (SEQ ID NO:42)
TAAGTTATCACTAGAAATCACTTCTTTTTTATTTTGGTAATAATCCAGTCGGTAACAACGATCCAATCCTTTTTCAGTAGGATTT
TCTCGTTGAAGCCGAATTCTGCAGATATCCATCACACTGGCGGCCGCTCGAGCATGCATCTAGAGGGCCCAATTCGCCCTATAGT
GAGCGTATTACAATTCACTGGCCGTCGTTTTACA 3'.

Fragment 10 and Fragment 11, were purified using a QIAquick PCR Purification Kit (Qiagen, Valencia, Calif.).

For round 2 of the lower primer mutation, the template used was Fragment 10, the 262 bp product from MOD51U/PCR II FOR. The primers used were as follows:

```
MOD52U
5' CGA CAA CAA CTG GTA TGC GGA 3'    (SEQ ID NO:43)

PCR II FOR
5' CAG GAA ACA GCT ATG ACC 3'        (SEQ ID NO:44)
```

The product, Fragment 12, was a 272 bp product as follows:

5' CAGGAAACAGCTATGACCATGATTACGCCAAGCTTGGTACCGAGCTCGGATCCACTAGTAACGGCCGCCAGTGTGCTGGAAT (SEQ ID NO:45)
TCGGCTTGAAATCACTGTACGGATCAGAAGCCGTGCTCCATTTTTCGGGAGATGATTTATATTTGGTTAATCCTTTCTTTTCATG
AATATTAGAAATCCATGGTGAAAGAAAAGTTCTTTTATTTTTGACATCAACCGTATATCCTTCTACCTCTAATGAATCAGGGATT
CCGCATACCAGTTGTTGTCG 3'.

Also for round 2 of the lower primer mutation, the template used was Fragment 11, the 286 bp product from MOD51L/PCR II REV. The primers used were as follows:

```
MOD52L
5' TCC GCA TAC CAG TTG TTG TCG 3'    (SEQ ID NO:46)

PCR II REV
5' TGT AAA ACG ACG GCC AGT 3'        (SEQ ID NO:47)
```

The product, Fragment 13, was a 296 bp product as follows:

5' TCCGCATACCAGTTGTTGTCGAACGTAGTTGATCGCTCTCAGTCCATCCGTTTTTCTTGAGTTCGAAGATTTTTGTTTTAAT (SEQ ID NO:48)
TCTGGCAATTGTAAGTTATCACTAGAAATCACTTCTTTTTTATTTTGGTAATAATCCAGTCGGTAACAACGATCCAATCCTTTTT
CAGTAGGATTTTCTCGTTGAAGCCGAATTCTGCAGATATCCATCACACTGGCGGCCGCTCGAGCATGCATCTAGAGGGCCCAATT
CGCCCTATAGTGAGCGTATTACAATTCACTGGCCGTCGTTTTACA 3'.

Fragment 12 and Fragment 13 were purified with the QIAquick PCR Purification Kit (Qiagen, Valencia, Calif.).

For round 3 of the lower primer mutation, Fragment 12 was hybridized with Fragment 13. Additional PCR II FOR and PCR II REV primers were added. The product was 548 bp as follows:

```
5' CAGGAAACAGCTATGACCATGATTACGCCAAGCTTGGTACCGAGCTCGGATCCACTAGTAACGGCCGCCAGTGTGCTGGAAT        (SEQ ID NO:49)

TCGGCTTGAAATCACTGTACGGATCAGAAGCCGTGCTCCATTTTTCGGGAGATGATTTATATTTGGTTAATCCTTTCTTTTCATG

AATATTAGAAATCCATGGTGAAAGAAAAGTTCTTTTATTTTTGACATCAACCGTATATCCTTCTACCTCTAATGAATCAGGGAT

TCCGCATACCAGTTGTTGTCGAACGTAGTTGATCGCTCTCAGTCCATCCGTTTTTCTTGAGTTCGAAGATTTTTGTTTTAATTCT

GGCAATTGTAAGTTATCACTAGAAATCACTTCTTTTTTATTTTGGTAATAATCCAGTCGGTAACAACGATCCAATCCTTTTTCAG

TAGGATTTTCTCGTTGAAGCCGAATTCTGCAGATATCCATCACACTGGCGGCCGCTCGAGCATGCATCTAGAGGGCCCAATTCGC

CCTATAGTGAGCGTATTACAATTCACTGGCCGTCGTTTTACA 3'.
```

The underlined sequence in SEQ ID NO:49 indicates the 153 base amplicon sequence which is herein designated SEQ ID NO:89.

The product was gel purified with the QIAquick Gel Extraction Kit and cloned using the Original TA Cloning Kit (Invitrogen Corporation, Carlsbad, Calif.). All of the clones were sequenced with both forward and reverse primers in duplicate. Clone 1 was selected because it had the mutated sequence of the 548 bp product (SEQ ID NO:49) and the rest of the sequence remained unaltered. The Qiagen Plasmid Mini Purification Kit (Qiagen, Carlsbad, Calif.) was used to purify the plasmid DNA, the final clone.

Cultures of competent INVαF' *E. coli* (Invitrogen Corporation, Carlsbad, Calif.) were transformed according to the manufacturer's instructions. The transformed cultures were plated on LB plates comprising 100 µg/ml ampicillin and 1.6 mg X-Gal. White colonies were chosen, screened with PCR, and sequenced. The clone that comprised the DNA sequence of the final clone was chosen, grown overnight in a LB broth culture containing 100 µg/ml ampicillin. Plasmid purification was performed on the broth culture with the Qiagen Plasmid Mini Purification Kit (Qiagen, Carlsbad, Calif.). The plasmid DNA was resequenced for confirmation. This plasmid DNA was then used for the next mutation.

The mutated sequences were identical to the wild type sequences in length, base composition and location. Mutated sequences were chosen that had optimal primer characteristics without matching any known naturally occurring DNA sequences. The mutated sequences were checked with a nucleotide BLAST search to confirm the uniqueness of the sequences. See http://www.ncbi.nlm.nih.gov/BLAST/. The final product is the IPC nucleic acid molecule of the present invention, a cloned fragment of DNA having a unique sequence that can be used in any probe-based PCR assay with specific primers and probes. Additionally, the IPC nucleic acid molecule of the present invention may be used with fluorescence resonance energy transfer (FRET), Scorpions, and Molecular Beacons assays. See Szollosi, et al. (1998) Cytometry 34(4):159–179; Schweitzer and Kingsmore (2001) Curr. Opin. Biotechnol. 12(1):21–27; and Antony and Subramaniam (2001) J. Biomol. Struct. Dyn. 19(3):497–504, which are herein incorporated by reference.

As provided in Example 4 herein, the IPC nucleic acid molecule of the present invention may be used to develop an internal positive control ribonucleic acid molecule for reverse-transcriptase PCR reactions. The IPC nucleic acid molecules for use in reverse transcriptase PCR applications are herein referred to as "RT-IPC nucleic acid molecules". As provided herein, the RT-IPC nucleic acid molecule was sensitive to a variety of known reverse transcriptase inhibitors, as well as, several PCR inhibitors, including heparin, EDTA, glycerol, guanidine thiocyanate, DMSO, SDS, guanidine hydrochloride, and formamide. Thus, the RT-IPC nucleic acid molecule of the present invention is may be used to monitor inhibitors of RT-PCR applications and build confidence in negative results obtained with agent specific assays.

As provided in Example 4, purified IPC plasmid DNA was linearized with the restriction enzyme SpeI. The T7 promoter on the pCR 2.1 vector (which contains the IPC DNA insert) was then used to in vitro transcribe the IPC RNA, using methods known in the art. The resultant IPC RNA, RT-IPC nucleic acid molecule, can be used in reverse transcription PCR (RT-PCR) assays to monitor inhibition in the same capacity that the IPC nucleic acid molecule of the present invention is used for PCR assays.

RT-PCR of RNA templates uses two enzymes, reverse transcriptase and Taq Polymerase. RT-PCR thus has two weak points at which inhibition can occur, making it even more susceptible to inhibition than PCR. The RT-IPC nucleic acid molecule may be used to detect inhibitors of Taq polymerase as well as inhibitors of reverse transcriptase.

The RT-IPC nucleic acid molecule of the present invention includes RNase-resistant RT-IPC nucleic acid molecules as known in the art. RNase-resistant nucleic acid molecules include complexes of MS2 bacteriophage coat proteins and RNA molecules produced in *Escherichia coli* by the induction of an expression plasmid that encodes the coat protein and the RNA sequence. The RNA sequences are protected from RNase digestion within the bacteriophage-like complexes (Ambion, Inc., Austin, Tex.). RNase-resistant RT-IPC nucleic acid molecules according to the present invention allow use of the RT-IPC nucleic acid molecules throughout an entire assay procedure, i.e. from extraction of the RNA to amplification. In addition, RNase-resistant RT-IPC nucleic acid molecules according to the present invention have greater stability. See Eisler, D. L. et al. (2004) J. Clin. Microbiol. 42(2):841–844; Bressler, A. M. and Nolte, F. S. (2004) J. Clin Microbiol. 42(3):987–491; Beld, M. et al. (2004) J. Clin. Microbiol. 42(7):3059–3064, which are herein incorporated by reference.

The IPC and RT-IPC nucleic acid molecules of the present invention may be used in a probe-based nucleic acid diagnostic assay to determine the presence or absence of PCR inhibitors. An assay utilizing the IPC and RT-IPC nucleic acid molecules of the present invention can either be run by itself or multiplexed with any other diagnostic assay. The IPC and RT-IPC nucleic acid molecules of the present invention may be used as a control assay to trouble-shoot probe-based nucleic acid assay problems such as PCR assays. For example, the IPC and RT-IPC nucleic acid molecules of the present invention may be used to determine if a problem relates to the reagents, operator technique, or instrumentation.

The IPC nucleic acid molecule, RT-IPC nucleic acid molecule, or both may be multiplexed or used in conjunction with other assays for the detection of an organism based on the presence of a target nucleic acid molecule that is unique to the organism. For example, the IPC and RT-IPC nucleic acid molecules of the present invention may be used in conjunction with assays, known in the art, for organisms belonging to *Bacillus, Mycobacterium, Francisella, Brucella, Clostridium, Yersinia, Variola, Orthopox*, and *Burkholderia*. See e.g Fasanella, A. et al. (2003) J. Clin. Microbiol. 41(2):896–899 (*Bacillus anthracis*); Drago, L. et al. (2002) J. Clin Microbiol. 40(11):4399 (*Bacillus anthracis*); Espy, M. J. et al. (2002) Mayo Clin. Proc. 77(7): 624–628 (bioterrorism agents); Montenegro, S. H. et al. (2003) Clin. Infect. Dis. 36(l):16–23 (*Mycobacterium tuberculosis*); Johansson, A. et al. (2000) J. Clin. Microbiol. 38(11):4180–4185 (*Francisella tularensis*); Emanuel, P. A. et al. (2003) J. Clin. Microbiol. 41(2):689–693 (*Francisella tularensis*); Navarro, E. et al. (2002) FEMS Immunol. Med. Microbiol. 34(2):147–151 (*Brucella* spp); Bricker, B. J. (2002) Vet. Microbiol. 90(1–4):435–446 (*Brucella*); Lindstrom, M. et al. (2001) Appl. Environ. Microbiol. 67(12): 5694–5699 (*Clostridium botulinum*); Lindler, L. E. et al. (2001) J. Clin. Microbiol. 39(10):3649–3655 (*Yersinia pestis*); Radnedge, L. et al. (2001) Appl. Environ. Microbiol. 67(8):3759–3762 (*Yersinia pestis*); Czemy, C. P. et al. (1997) Arch. Virol. Suppl. 13:13–24 (orthopox virus); Epsy, M. J. et al. (2002) J. Clin. Microbiol. 40(6):1985–1988 (smallpox); Meyer, H. et al. (2002) J. Vet. Med. B. Infect. Dis. Vet. Public Health 49(1):17–19 (*variola*); Meyer, H. et al. (1997) J. Virol. Methods 64(2):217–221 (orthopox); Woo, P. C. et al. (2002) Diagn. Microbiol. Infect. Dis. 44(2): 143–149 (*Burkholderia*); and Vermis, K. et al. (2002) J. Med. Microbiol. 51(11):937–940 (*Burkholderia*), which are herein incorporated by reference.

As used herein, "nucleic acid molecule", "polynucleotide", and "oligonucleotide" are used interchangeably to refer DNA and RNA molecules of natural or synthetic origin which may be single-stranded or double-stranded, and represent the sense or antisense strand. The nucleic acid molecules of the present invention may contain known nucleotide analogs or modified backbone residues or linkages, and any substrate that can be incorporated into a polymer by DNA or RNA polymerase. Examples of such analogs inlude phosphorothioates, phosphoramidates, methyl phosphonates, chiral-methyl phosphonates, 2-O-methyl ribonucleotides, peptide-nucleic acids (PNAs), and the like.

In preferred embodiments, the IPC and RT-IPC nucleic acid molecules of the present invention are isolated. As used herein, "isolated" refers to a nucleic acid molecule that is isolated from its native environment. An "isolated" nucleic acid molecule may be substantially isolated or purified from the genomic DNA of the species from which the nucleic acid molecule was obtained. An "isolated" polynucleotide may include a nucleic acid molecule that is separated from other DNA segments with which the nucleic acid molecule is normally or natively associated with at either the 5' end, 3' end, or both.

The IPC and RT-IPC nucleic acid molecules of the present invention may be in their native form or synthetically modified. The IPC and RT-IPC nucleic acid molecules of the present invention may be single-stranded (coding or antisense) or double-stranded, and may be DNA (genomic, cDNA or synthetic) or RNA molecules. RNA molecules include mRNA molecules, which contain introns and correspond to a DNA molecule in a one-to-one manner, and mRNA molecules, which do not contain introns. The IPC and RT-IPC nucleic acid molecules of the present invention may be linked to other nucleic acid molecules, support materials, reporter molecules, quencher molecules, or a combination thereof. Other nucleic acid molecules include promoters, polyadenylation signals, additional restriction enzyme sites, multiple cloning sites, other coding segments, and the like. It is therefore contemplated that a nucleic acid fragment of almost any length may be employed, with the total length preferably being limited by the ease of preparation and use in the intended recombinant DNA or PCR protocol. In some embodiments of the present invention, nucleic acid sequences comprising the IPC oligonucleotide described herein are contemplated.

The IPC and RT-IPC nucleic acid molecules of the present invention may be readily prepared by conventional methods known in the art, for example, directly synthesizing the nucleic acid sequence using methods and equipment known in the art such as automated oligonucleotide synthesizers, PCR technology, recombinant DNA techniques, and the like.

The IPC and RT-IPC nucleic acid molecules of the present invention may contain a label such as quencher molecule and a reporter molecule. A wide variety of labels and conjugation techniques are known by those skilled in the art and may be used in various nucleic acid and amino acid assays employing the IPC and RT-IPC nucleic acid molecules of the present invention. As used herein a "label" or a "detectable moiety" is a composition that is detectable by spectroscopic, photochemical, biochemical, immunochemical, or chemical means. A "labeled" nucleic acid molecule comprises a bound label such that the presence of the nucleic acid molecule may be detected by detecting the presence of the label bound to thereto. The label may be bound to the nucleic acid molecule via a covalent bond, such as a chemical bond, or a noncovalent bond, such as ionic, van der Waals, electrostatic, or hydrogen bonds. Methods known in the art for producing labeled hybridization or PCR probes for detecting sequences related to polynucleotides may be used and include oligolabeling, nick translation, end-labeling or PCR amplification using a labeled nucleotide, and the like, preferably end-labeling. Suitable reporter molecules and quencher molecules that may be used include radionucleotides, enzymes, fluorescent, chemiluminescent, or chromogenic agents as well as substrates, cofactors, inhibitors, magnetic particles, and the like. In preferred embodiments, a fluorescent reporter molecule and quencher molecule are used.

As used herein, a "nucleic acid probe" and "probe" refers to a nucleic acid molecule that is capable of binding to a target nucleic acid molecule having a sequence that is complementary to the sequence of the nucleic acid probe. A probe may include natural or modified bases. See e.g MPEP 2422, $8^{th}$ ed., which is herein incorporated by reference. The nucleotide bases of the probe may be joined by a linkage other than a phosphodiester bond, so long as the linkage does not interfere with the ability of the nucleic acid molecule to bind a complementary nucleic acid molecule. The probe may bind a target sequence that is less than 100% complementary to the probe sequence and such binding depends upon the stringency of the hybridization conditions. The presence or absence of the probe may be detected to determine the presence or absence of a target sequence or subsequence in a sample. The probe may contain a label whose signal is detectable by methods known in the art. As used herein a "signal" is a measurable characteristic. Where the label is a reporter molecule and a quencher molecule, the signal may increase or decrease upon dissociation of reporter molecule and the quencher molecule. For example, if the reporter molecule is a fluorophore, separation of the quencher from the fluorophore will generate a detectable signal due to an increase in light energy emitted by the fluorophore in response to illumination.

As used herein, a "target" nucleic acid molecule may be any nucleic acid molecule, the presence and/or amount of which is desired to be known. In some embodiments, the sequence of the target nucleic acid molecule is known. In some embodiments, e.g., mutation detection, the sequence of the target nucleic acid molecule may be a sequence that is suspected of having alterations, i.e. differences, from a reference nucleic acid sequence. In these embodiments, the sequence of the target nucleic acid molecule may or may not be known, and the "reference nucleic acid sequence" is a known nucleic acid sequence to which the sequence of the target nucleic acid molecule may be compared. The alteration in the target nucleic acid molecule may be in a single nucleotide base or more than a single nucleotide base. Such an alteration may be a known polymorphic alteration, such as a single nucleotide polymorphism.

The present invention further provides kits for use with nucleic acid hybridization assays such as PCR amplification and PCR assays, including TaqMan® based assays, fluorescence resonance energy transfer (FRET), Scorpions, and Molecular Beacons assays. See Szollosi, et al. (1998) Cytometry 34(4):159–179; Schweitzer and Kingsmore (2001) Curr. Opin. Biotechnol. 12(1):21–27; and Antony and Subramaniam (2001) J. Biomol. Struct. Dyn. 19(3): 497–504, which are herein incorporated by reference. Such kits comprise the IPC nucleic acid molecule, RT-IPC nucleic acid molecule, or both, and one or more components necessary for performing the assay. Components may be compounds, reagents, containers, instructions and/or equipment.

The kits may be used for any one or more of the uses described herein, and, accordingly, may contain instructions for any one or more of the following uses: determining whether a target nucleic acid sequence is present in a sample, detecting a target nucleic acid sequence, quantifying a target nucleic acid sequence, comparing target nucleic acid sequence to a reference sequence, determining genotype, determining allele composition of a target nucleic acid, detecting and/or quantifying multiple nucleic acid sequences, and use of the methods in conjunction with nucleic acid amplification techniques.

The kits of the invention comprise one or more containers comprising any combination of the components or reagents described herein. For example, in one embodiment, the kit comprises the IPC nucleic acid molecule, RT-IPC nucleic acid molecule, or both and a set of primers and probes for conducting an assay for a target nucleic acid molecule. The kit may further include at least one label and at least one substrate or for producing a signal. The kit may further include deoxynucleoside triphosphates and/or ribonucleoside triphosphates. The kit may further include one or more suitable buffers for conducting the given assay. Each component of the kit can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the present invention for the intended nucleic acid detection and/or quantification, and/or, as appropriate, for using the detection and quantification methods in conjunction with amplification techniques. The instructions included with the kit generally include information as to reagents (whether included or not in the kit) necessary for practicing the methods of the presentation invention, instructions on how to use the kit, and/or appropriate reaction conditions.

As used herein, "sequence identity" in the context of two or more nucleic acid molecules, refers to two or more sequences or subsequences that are the same or have a specified percentage of nucleotide bases that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. The percentage of sequence identity may be calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Methods of alignment of sequences for comparison are well-known in the art. See e.g. Smith & Waterman (1981) Adv. Appl. Math. 2:482; Needleman & Wunsch (1970) J. Mol. Biol. 48:443; and Pearson & Lipman (1988) PNAS USA 85:2444, which are herein incorporated by reference. Alignment may be conducted using computer programs such as GAP, BESTFIT, FASTA, and TFASTA in the Wisconsin Genetics Software Package (Genetics Computer Group, 575 Science Dr., Madison, Wis.), or manually by visual inspection. See also Feng & Doolittle (1987) J. Mol. Evol. 35:351–360; Higgins & Sharp (1989) CABIOS 5:151–153; and Devereaux et al. (1984) Nuc. Acids Res. 12:387–395, which are herein incorporated by reference.

Alternatively, BLAST and BLAST 2.0 algorithms may be used to determine the sequence identity of two or more sequences. See Altschul et al. (1977) Nuc. Acids Res. 25:3389–3402 and Altschul et al. (1990) J. Mol. Biol. 215:403–410, which are herein incorporated by reference. BLAST analyses are publicly available through the National Center for Biotechnology Information at http://www.ncbi.nlm.nih.gov/.

As provided herein, the IPC nucleic acid molecules of the present invention include nucleic acid molecules that have at least about 70% identity, preferably about 80% identity or more, more preferably about 90% identity or more, more preferably about 95% identity or more, over the 548 bp region set forth in SEQ ID NO:49. Nucleic acid molecules that have sequences that have at least about 70% identity to SEQ ID NO:49 are "substantially identical" to SEQ ID NO:49.

As provided in the Examples below, a plasmid containing the IPC nucleic acid molecule of the present invention was used to obtain an IPC RNA having SEQ ID NO:90, which is the complementary sequence from nucleotide position 55 to 508 of SEQ ID NO:49.

```
5' GGGCGAAUUGGGCCCUCUAGAUGCAUGCUCGAGCGGCCGCCAGUGUGAUGGAUAUCUGCAGAAUUCGGCUUCAACGAGAAAA    (SEQ ID NO:90)

UCCUACUGAAAAAGGAUUGGAUCGUUGUUACCGACUGGAUUAUUACCAAAAUAAAAAAGAAGUGAUUUCUAGUGAUAACUUACAA

UUGCCAGAAUUAAAACAAAAAUCUUCGAACUCAAGAAAAACGGAUGGACUGAGAGCGAUCAACUACGUUCGACAACAACUGGUAU

GCGGAAUCCCUGAUUCAUUAGAGGUAGAAGGAUAUACGGUUGAUGUCAAAAAUAAAAGAACUUUUCUUUCACCAUGGAUUUCUAA

UAUUCAUGAAAAGAAAGGAUUAACCAAAUAUAAAUCAUCUCCCGAAAAUGGAGCACGGCUUCUGAUCCGUACAGUGAUUUCAAGC

CGAAUUCCAGCACACUGGCGGCCGUUACUAG 3'
```

SEQ ID NO:90 contains the RT-IPC amplicon which is underlined and is herein designated as SEQ ID NO:91, which is the complementary sequence from nucleotide position 105 to 257 of SEQ ID NO:89.

The reverse transcription-PCR target within SEQ ID NO:90 begins at nucleotide position 105 and ends at nucleotide 257. As provided herein, the RT-IPC nucleic acid molecules of the present invention include nucleic acid molecules that have at least about 70% identity, preferably about 80% identity or more, more preferably about 90% identity or more, more preferably about 95% identity or more, over the 153 base region of SEQ ID NO:90. In some embodiments, the RT-IPC nucleic acid molecules of the present invention include nucleic acid molecules that have at least about 70% identity, preferably about 80% identity or more, more preferably about 90% identity or more, more preferably about 95% identity or more, over the 453 base region of SEQ ID NO:90.

In preferred embodiments, the IPC and RT-IPC nucleic acid molecules of the present invention contains at least 80 consecutive bases of SEQ ID NO:89 or its complement. In some embodiments, the IPC or RT-IPC nucleic acid molecules comprise SEQ ID NO:89 or its complement.

Nucleic acid molecules that have sequences that have at least about 70% identity to a given sequence are "substantially identical" to the given sequence. As used herein, the phrase "selectively (or specifically) hybridizes to" refers to the binding, duplexing, or hybridizing of a nucleic acid molecule to a particular nucleotide sequence only in a sample comprising other nucleic acid molecules under stringent hybridization to moderate hybridization conditions. For selective or specific hybridization, a positive signal is at least about 2 times, preferably about 5 times, more preferably about 10 times the background hybridization. Stringent hybridization conditions are about 5° C. below the thermal melting temperature (Tm) of the probe to about 10° C. below Tm. Moderate hybridization conditions are about 10° C. below the thermal melting temperature (Tm) of the probe to about 20° C. to about 25° C. below Tm.

The following examples are intended to illustrate but not to limit the invention.

EXAMPLE 1

Mutagenic Process

Figure 2:
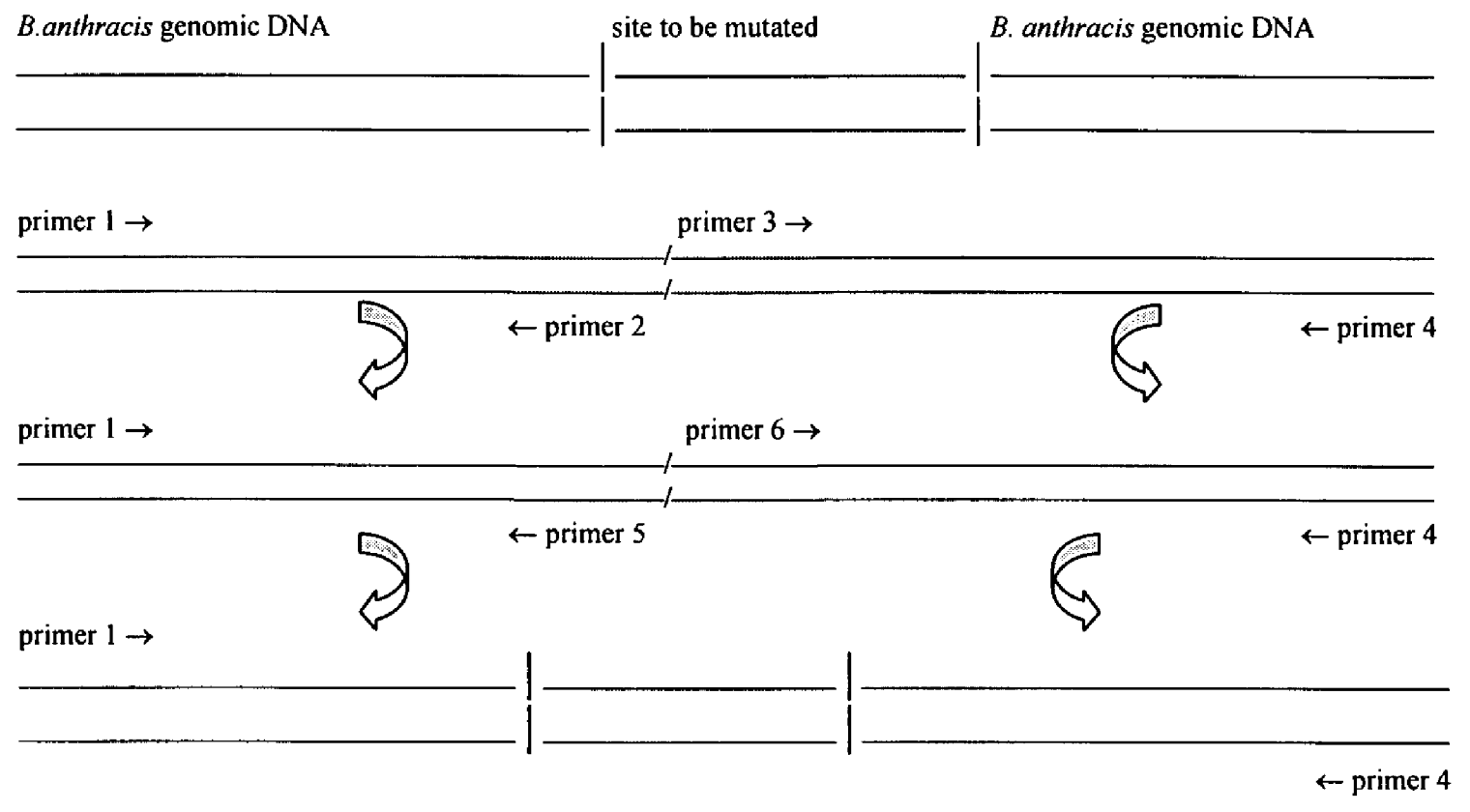

FIG. 2 schematically shows the site-directed mutagenesis process used to generate the IPC nucleic acid molecule of the present invention. As shown, the first two sets of PCR reactions allowed ½ of the mutated sequence to be incorporated into the generated PCR fragments. Template DNA was placed in one reaction with primers 1 and 2, and another reaction with primers 3 and 4. The next two sets of PCR reactions allowed for full incorporation of the mutated sequence into the PCR products. In one reaction, the primer set 1 and 2 generated DNA fragment was used as a template for amplification with primers 1 and 5. The other reaction used the primer set 3 and 4 generated DNA fragment as a template for amplification with primers 4 and 6. In the final round, both fragments from primers 1 and 5 and from primers 4 and 6 were used as primers for each other in an overlap extension reaction. Partway through the PCR, primers 1 and 4 were added to the reaction. The final product was one DNA fragment that fully incorporated the mutated sequence.

After completing the mutagenesis of all three sites, the sequence was verified. Clone 1, the final clone chosen, was re-sequenced. Both, the forward strand and the reverse strand in duplicate with the dideoxy sequencing method using the Big Dye Sequencing Kit (Applied Biosystems, Foster City, Calif.).

EXAMPLE 2

Effect of Inhibitors on IPC

The effect of three inhibitors, hemoglobin, heparin, and EDTA, on the IPC nucleic acid molecule of the present invention was tested. The IPC DNA was titrated to use the smallest amount possible to still obtain consistent results, yet make the assay very sensitive to inhibition. Using the Smart Cycler® (Cepheid, Sunnyvale, Calif.) 1 fg of IPC DNA was found to be optimal for the methods herein. The reagents used were Idaho Technology PCR Reagents (Idaho Technology, Idaho Falls, Id.), which include the 10× buffer with 30 mM $MgCl_2$ and 10×dNTP. 5×SC buffer, an additive recommended by Cepheid (Cepheid, Sunnyvale, Calif.), the manufacturers of the Smart Cycler®, and Platinum Taq DNA Polymerase (Invitrogen, Carlsbad, Calif.), was also used. The PCR was started with 2-minute activation at 95° C. and then 45 cycles of 95° C. for 1 second and 65° C. for 20 seconds. The assay was tested against these three inhibitors using probes labeled with two different reporter dyes, FAM and ROX. The quencher on both of these probes was TAMRA. Biosearch Technologies, Novato, Calif., manufactured the probes.

A. Hemoglobin

The effect of hemoglobin was initially tested with a 10-fold dilution series from 6 µg/µl to 0.0006 µg/µl final concentration in a 25 µl reaction volume and then tested with 2-fold dilution series from 0.06 µg/µl to 0.0006 µg/µl final concentration.

With both reporter dyes, FAM and ROX, 0.06 µg/µl was partially inhibitory. Inhibition was completely relieved at 0.03 µg/µl.

B. Heparin

The effect of heparin was initially tested with 10-fold dilution series from 2 Units/µl to 0.00002 Units/µl final concentration in a 25 μl reaction volume and then tested with 2-fold dilution series from 0.002 Units/μl to 0.00025 Units/μl final concentration.

Heparin was completely inhibitory at 0.0005 Units/μl and inhibition was completely relieved at 0.00025 Units/μl.

C. EDTA

The effect of EDTA was tested with 2-fold dilution series from 5 mM to 0.156 mM final concentration in a 25 μl reaction.

EDTA was completely inhibitory at 5 mM and 2.5 mM. With the FAM probe, inhibition was completely relieved at 1.25 mM. With the ROX probe, 1.25 mM was partially inhibitory and inhibition was not completely relieved until 0.625 mM.

EXAMPLE 3

Limit of Detection

To determine whether the IPC nucleic acid molecule of the present invention affects the limit of detection of a given assay, the following was conducted.

The IPC nucleic acid molecule was duplexed with all of the assays that we currently use on the Smart Cycler®. The IPC nucleic acid molecule was labeled with ROX and the primary assay probes were labeled with FAM. Ten-fold serial dilutions were performed on all genomic DNA samples for the primary assays. The limit of detection was tested in triplicate for each assay.

A. Assay for *Bacillus anthracis*

The primer set used was BAPA3U/5L and the probe was BAPA3P2A.

```
BAPA3U:
5' TTCAAGTTGTACTGGACCGATTCTC 3'      (SEQ ID NO:50)

BAPA5L:
5' TCCATCATTGTCACGGTCTGG 3'          (SEQ ID NO:51)

BAPA3P2A:
5' CCGTAGGTCCAGCACTTGTACTTCGCTT 3'   (SEQ ID NO:52)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 65° C. for 20 seconds. Testing was performed with and without the IPC assay. One fg of IPC DNA was used. Limit of detection of the PA assay was 10 fg in both cases.

B. Assay for *Bacillus anthracis*

The primer set used was BACAPBU2/L2 and the probe was BACAPBP2.

```
BACAPBU2:
5' GCTGACCAATCTAAGCCTGC 3'           (SEQ ID NO:53)

BACAPBL2:
5' GGCAAAACATCCCTAGCAAA 3'           (SEQ ID NO:54)

BACAPBP2:
5' TTGTAATTATGAATTGCCGCCCTGACC 3'    (SEQ ID NO:55)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. Five fg of IPC DNA were used. Limit of detection of the CAPB assay was 100 fg without IPC and 1 pg with IPC.

C. Assay for *Brucella*

The primer set used was BROMPF394/R474 and the probe was BROMP25-420S.

```
BROMPF394:
5' AACAAGGCCAAGACCAGCACC 3'          (SEQ ID NO:56)

BROMPR474:
5' CTGGAAGTTCCAGCCAGCAA 3'           (SEQ ID NO:57)

BROMP25-420S:
5' CAGCATCAAGCCTGACGATTGGAAGG 3'     (SEQ ID NO:58)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection of the *Brucella* assay was 1 fg in both cases. Without IPC there was 1 hit out of 3 for 100 ag.

D. Assay for *Clostridium botulinum*

The primer set used was CBOTA4U/4L and the probe was CBOTA4P2A.

```
CBOTA4U:
5' GATATAGGCTTTATAGGATTTCATCAG 3'    (SEQ ID NO:59)

CBOTA4L:
5' CCTTTCTCCCCATCCATC 3'             (SEQ ID NO:60)

CBOTA4P2A:
5' TCCCATGAGCAACCCAAAGTCCTACT 3'     (SEQ ID NO:61)
```

The reaction mix included 10×PCR buffer with 4 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection of the *C. botulinum* assay was 100 fg in both cases. Without IPC there was 1 hit out of 3 for 10 fg.

E. Assay for *Yersinia pestis*

The primer set used was YPPLA3U/3L and the probe was YPPLAP3F.

```
YPPLA3U:
5' GGTACCGTAATTAACGCTGG 3'           (SEQ ID NO:62)

YPPLA3L:
5' GTCTGAGTACCTCCTTTGCC 3'           (SEQ ID NO:63)
```

-continued

YPPLAP3F:
5' ACCTAATGCCAAAGTCTTTGCGGA 3'  (SEQ ID NO:64)

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (2 out of 3) and without (2 out of 3) IPC was 1 fg F. Assay for *Bacillus anthracis*

The primer set used was BACAPB4U/4L and the probe was BACAPBP1S.

BACAPB4U:
5' CAGATAATGCATCGCTTGCTTTAG 3'  (SEQ ID NO:65)

BACAPB4L:
5' GGATGAGCATTCAACATACCACG 3'  (SEQ ID NO:66)

BACAPBP1S:
5' CAGAGGCTCTTGGGATTGATGAGGAAACA 3'  (SEQ ID NO:67)

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with IPC was 100 fg and without IPC was 10 fg (2 out of 3)

G. Assay for *Bacillus anthracis*

The primer set used was BAVRRA3U/3L and the probe was BAVRRA3P1S.

BAVRRA3U:
5' AAATGTATGAATCAAACGAAACGC 3'  (SEQ ID NO:68)

BAVRRA3L:
5' CAGGGCTTACAGATTGAACG 3'  (SEQ ID NO:69)

BAVRRA3P1S:
5' CGGTGCAGCAACTACAGCAGCA 3'  (SEQ ID NO:70)

The reaction mix included 10×PCR buffer with 3 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 10 fg.

H. Assay for *Francisella tularensis*

The primer set used was FTTULU1/L1 and the probe was FTTULP1F.

FTTULU1:
5' CAGCATACAATAATAACCCACAAGG 3'  (SEQ ID NO:71)

FTTULL1:
5' TCAGCATACTTAGTAATTGGGAAGC 3'  (SEQ ID NO:72)

FTTULP1F:
5' TTACAATGGCAGGCTCCAGAAGGTTC 3'  (SEQ ID NO:73)

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 55° C. for 20 seconds. Testing was performed with and without the IPC assay. One fg of IPC DNA was used. Limit of detection with IPC was 10 fg (2 out of 3) and without IPC was 1 fg.

I. Assay for *Yersinia pestis*

The primer set used was YPPIMU1/L1 and the probe was YPPIMP1R.

YPPIMU1:
5' AGTGGCCTTGCAGAAAAAA 3'  (SEQ ID NO:74)

YPPIML1:
5' GTAAACTCGGTTTGCTTGAAG 3'  (SEQ ID NO:75)

YPPIMP1R:
5' TGTCTGTTTCCCATAGATGCCATGA 3'  (SEQ ID NO:76)

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (3 out of 3) and without IPC (1 out of 3) was 1 fg.

J. Assay for *Orthopox* sp.

The primer set used was OPSPF89/R219 and the probe was Op-p143S.

OPSPF89:
5' GATGATGCAACTCTATCATGTA 3'  (SEQ ID NO:77)

OPSPR219:
5' GTATAATTATCAAAATACAAGACGTC 3'  (SEQ ID NO:78)

Op-p143S:
5' AGTGCTTGGTATAAGGAG 3'  (SEQ ID NO:79)

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 100 fg.

K. Assay for *Francisella tularensis*

The primer set used was FOPAF708/R846 and the probe was FtFOPA765S.

```
FOPAF708:
5' CTGGTTTAACATGGTTCTTTGGTG 3'        (SEQ ID NO:80)

FOPAR846:
5' CCAGCAGGTAAAACATACTTAGACTCA 3'     (SEQ ID NO:81)

FtFOPA765S:
5' TCCAGGATAATGGTGCGACTACAGCTGC 3'    (SEQ ID NO:82)
```

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 10 fg.

L. Assay for *Variola*

The primer set used was J7R3U/3L and the probe was VARJ7R3p.

```
J7R3U:
5' CATCATTGGCGGTTGATTTA 3'            (SEQ ID NO:83)

J7R3L:
5' TCATCTGGAGAATCCACAACA 3'           (SEQ ID NO:84)

VARJ7R3p:
5' CAAGACGTCGGGACCAATTACTAATA 3'      (SEQ ID NO:85)
```

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (2 out of 3) and without (3 out of 3) IPC was 100 ag.

M. Assay for *Burkholderia*

The primer set used was BPISO2F1/R1 and the probe was BMISO2PF3.

```
BPISO2F1:
5' CTCGAGGTGGAGAATGCCC 3'             (SEQ ID NO:86)

BPISO2R1:
5' CGCTCGGAGATGTTGACCTTC 3'           (SEQ ID NO:87)

BMISO2PF3:
5' TGGCCGAAGCAATGCTCGATATGG 3'        (SEQ ID NO:88)
```

The reaction mix included 10×PCR buffer with 5 mM MgCl$_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection without IPC was 10 ag. This assay did not work in the presence of the IPC.

EXAMPLE 4

Internal Positive Control for Reverse Transcriptase Based Nucleic Acid Assays

Generally, to create a RT-IPC nucleic acid molecule according to the present invention, purified IPC plasmid DNA obtained according to the Examples above was linearized with the restriction enzyme SpeI. The T7 promoter on the pCR 2.1 vector (which contains the IPC DNA insert) was then used to in vitro transcribe the IPC RNA (SEQ ID NO:91) using methods known in the art. See Milligan, et al., (1987) Nucleic Acids Res. 15 (21): 8783–8798, which is herein incorporated by reference. The resultant IPC RNA (SEQ ID NO:89) sequence contains the RT-IPC nucleic acid molecule (SEQ ID NO:90).

A. Linearization of IPC Plasmid.

The plasmid containing the IPC nucleic acid molecule was linearized by restriction digest in order to provide a linear template for in vitro transcription of RNA. Briefly, 10 μg of IPC plasmid was cut in a restriction digest with 10 U of Spe1 restriction endonuclease (Invitrogen, Carlsbad, Calif.) in a restriction digest reaction in which the following reagents were added to a 1.7 ml microcentrifuge tube to a total volume of 40 μl:

10 μl molecular biology grade (MBG) water (Quality Biological, Gaithersburg, Md.)
4 μl 10× Buffer (Invitrogen, Carlsbad, Calif.)
25 μl IPC plasmid DNA (Sephadex® G50 purified, amount of DNA about 10 μg)
0.2 μl 200 mg/ml BSA (Invitrogen, Carlsbad, Calif.)
1 μl Spe1 (Invitrogen, Carlsbad, Calif.)

The reagents were mixed by gently flicking the bottom of the 1.7 ml microcentrifuge tube, centrifuged briefly, and placed in a 37° C. water bath. After a 1 hour incubation, the microcentrifuge tube was transferred to a 70° C. heat block and incubated for 15 minutes to inactive the Spe1 restriction endonuclease.

B. Agarose Gel Electorphoresis of Linearized IPC Nucleic Acid Molecule

A 1% agrose gel was prepared by adding 0.5 g of molecular biology grade agarose (Invitrogen, Carlsbad, Calif.) to 50 ml of 1×TAE buffer (Invitrogen, Carlsbad, Calif.) and microwaving for 2 minutes to dissolve the agarose. The agarose solution was poured into a gel casting template and a comb was inserted to form wells. The agarose solution was allowed to cool until a hardened gel formed. The gel was transferred to an electrophoresis box, and a solution of 1×TAE (Invitrogen, Carlsbad, Calif.) containing 0.5 μg/ml of ethidium bromide was poured into the gel box until it covered the gel.

Two μl of a 1:10 dilution of uncut plasmid, 0.5 μl of cut plasmid (Sephadex® G50 eluate of purified DNA prepared from an incomplete digestion), and plasmid linearized as described above were added to separate microcentifuge tubes. Various volumes of MBG water were added to each tube in order to bring the volume up in each tube to 9 μl. Next, 1 μl of 10× agarose gel loading buffer (Invitrogen, Carlsbad, Calif.) was added to each tube, and the tubes were mixed. The contents of each tube were added to separate wells of the 1% agarose gel. The gel electrophoresis box was connected to a power supply and the gel was electrophoresed at 125 volts until the dye present in the loading buffer had run three fourths the length of the gel. DNA present in the gel was observed by placing it on a UV light box, and a photo was taken. See FIG. 2.

Figure 3:
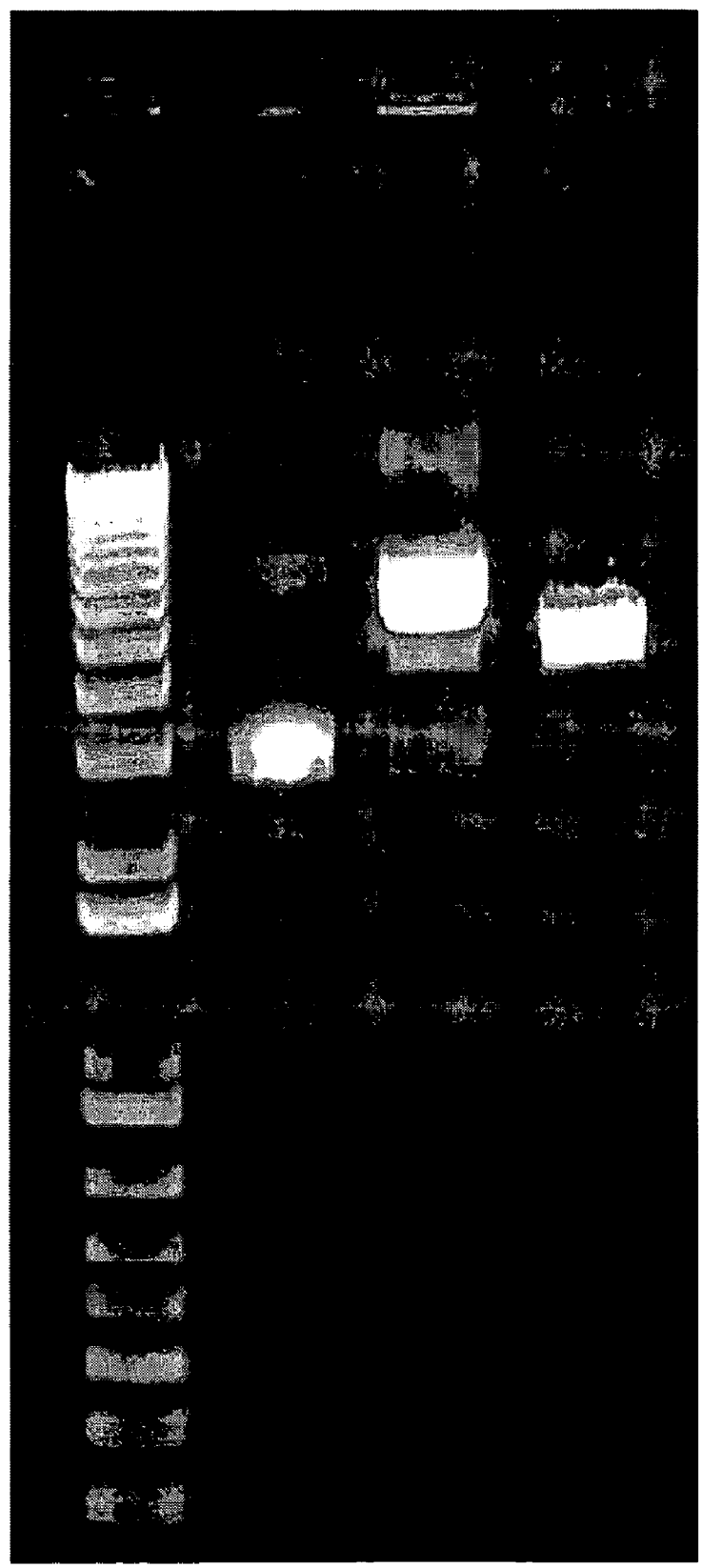

FIG. 3 shows the gel of Example 4B. Lane 1 is 3 μl (0.3 μg) a 1 kb DNA ladder, Lane 2 is 2 μl (0.2 μg) of a 1:10 dilution of uncut plasmid DNA, lane 3 is 0.5 μl (0.2 μg) of partially cut plasmid DNA that was purified by Sephadex® G50 purification, lane 4 is 1 μl (0.25 μg) of plasmid DNA linearized according to Example 4A.

C. In vitro Transcription from Spe1 Linearized IPC

The IPC RNA was transcribed from 1 μg of linear IPC by in vitro transcription using mMessage Machine™ with SuperRNAsin™ (Ambion, Austin, Tex.) at 37° C. following all the manufacturers instructions except that all components of the reaction were doubled resulting in a final volume of 40 μl. Briefly, the following Ambion reaction components were assembled in a 1.7 ml RNase free microcentrifuge tube (Ambion, Austin, Tex.) as shown below to a final volume of 40 μl:

6 μl water
4 μl 10× buffer
20 μl 2×rNTP
2 μl Extra GTP
4 μl (1.0 μg) Spe1 cut plasmid
4 μl 10×T7 enzyme The assembled reaction was mixed by gently flicking the bottom of the 1.7 ml microcentrifuge tube, and then placed in a 37° C. incubator. After a 1 hour incubation, 1 μl of 2 U/μl RNase-free DNase I (Ambion, Austin, Tex.) was added to the reaction. The microcentrifuge tube was mixed by gently flicking the bottom of the tube. The tube was centrifuged briefly then incubated at 37° C. for 15 minutes.

D. RNA Clean Up

RNA was purified from the Ambion mMessage Machine™ in vitro transcription reaction using a Qiagen RNeasy Mini Kit (Qiagen, Valencia, Calif.) following the manufacturers protocol. Briefly, 70 μl of RNase-free water were added to a 30 μl aliquot of the in vitro (DNase I treated) transcription reaction in order to bring the volume up to 100 μl. Next, 350 μl of Buffer RLT (Qiagen, Valencia, Calif.) was added to the tube and mixed thoroughly. Next 250 μl of 100% ethanol was added and the mixture was mixed thoroughly by pipetting the solution up and down several times. The sample was then loaded onto an RNeasy mini column and placed on top of a 2 ml collection tube. The cap on the column was closed, and the column with collection tube were centrifuged for 15 seconds at 8,000×g. The flow-through and collection tube were both discarded. The RNeasy column was placed into a new 2 ml collection tube, and 500 μl of Buffer RPE (Qiagen, Valencia, Calif.) was pipetted onto the RNeasy column. The tube was closed and centrifuged again as in the previous step. Again, the collection tube and flow-though were discarded. The Buffer RPE wash step was repeated again, and the column was inserted into a new collection tube. Next, 30 μl of RNase-free water was pippeted directly onto the silica-gel membrane in the RNeasy column. The cap was closed, and the column was centrifuged for 1 minute at 8,000×g in order to elute the RNA. The elution step was repeated with a new collection tube and another 30 μl of RNase-free water. The eluates collected after elution 1 and elution 2 were designated eluate 1 and eluate 2, respectively.

E. Agarose Gel Electrophoresis of Transcribed IPC RNA

A 50 ml 1% agarose gel was prepared by adding 0.5 g of molecular biology grade agarose to 50 ml of 1×TAE buffer and microwaving for 2 minutes to dissolve the agarose. The agarose solution was poured into a gel casting template and a comb was inserted to form wells. The agarose solution was allowed to cool until a hardened gel formed. The gel was transferred to an electrophoresis box, and a solution of 1×TAE containing 0.5 μg/ml ethidium bromide was poured into the gel box until it covered the gel.

Figure 4:
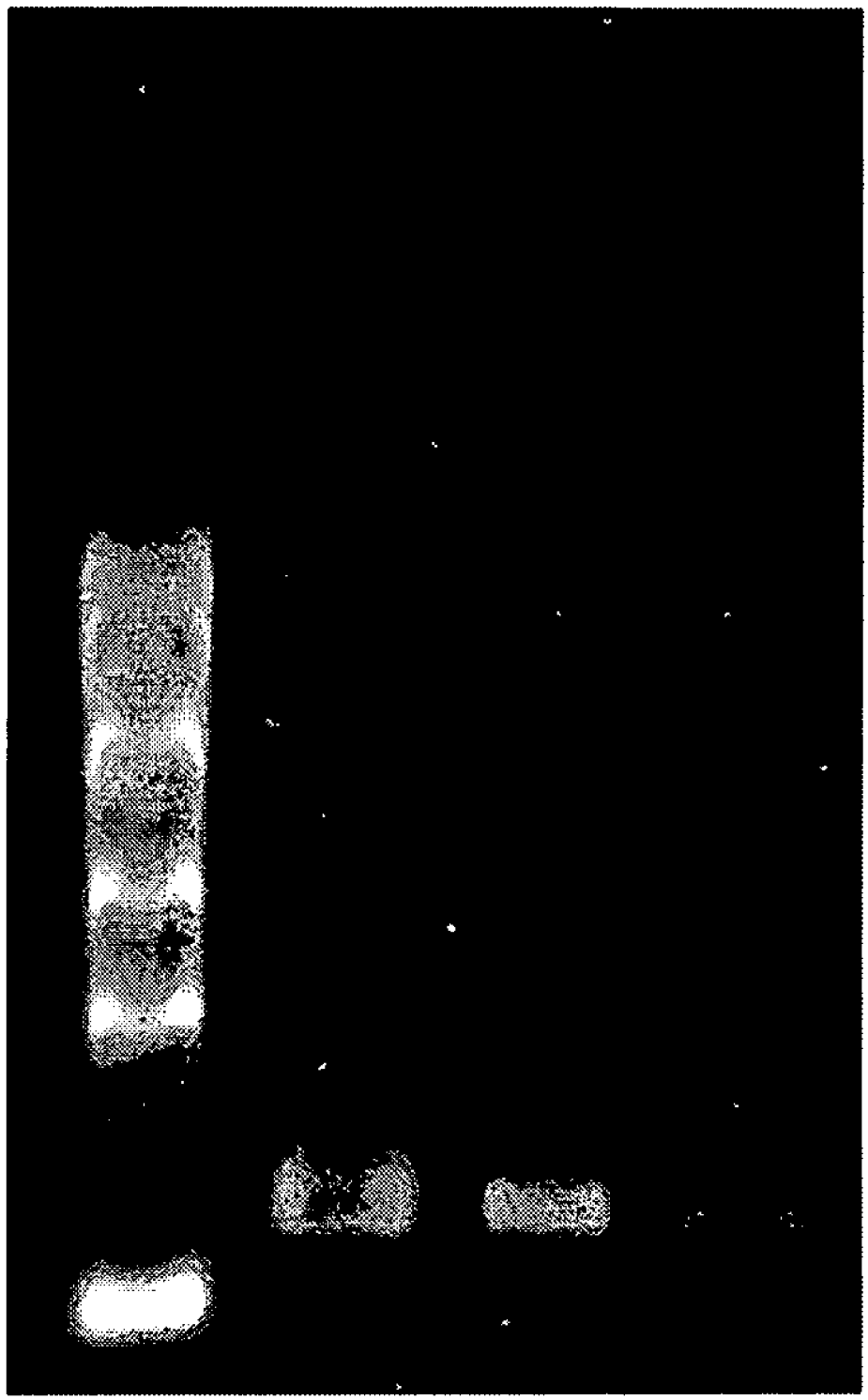

RNA samples were mixed with 2× Gel Loading Buffer II (Ambion, Austin, Tex.) and heated at 65° C. for 2 minutes to denature the RNA. FIG. 4 shows an agarose gel electrophoresis of denatured in vitro transcribed IPC RNA. Lane 1 is an RNA ladder, lane 2, is DNase treated transcription reaction, lane 3 is RNeasy eluate 1, and lane 4 is RNeasy eluate 2.

The agarose gel electrophoresis gel of FIG. 4 shows a single band of RNA at the expected size for the DNase treated transcription reaction (lane 2), RNeasy eluate 1 (lane 3), and RNeasy eluate 2 (lane 4), respectively. The gel also shows that the concentration of RNA in the original sample (prior to Qiagen purification) was slightly higher than the first Qiagen eluate. The concentration of RNA in the second Qiagen eluate was much less than the first. In addition, the gel shows that there was no degraded RNA.

F. RNA Quantification

RNA was quantified by measuring the $OD_{260}$ for duplicate samples comprising 2 μl of IPC RNA (RNeasy eluate) in total volume of 100 μl of RNase-free TE pH 8.0 (Quality Biological, Gaithersburg, Md.). The absorbance values were averaged and used to calculate the concentration of RNA using the formula: average absorbance at 260 nm×dilution factor×extinction coefficient=concentration of RNA; where the extinction coefficient for single stranded RNA was 40 μg RNA/ml. By this method the concentration of RNA was determined to be 0.169 μg/μl.

The total amount of RNA transcribed was 5.1 μg (0.169 μg/l×30 μl), which is sufficient for a large number of reverse transcription and PCR reactions.

G. Real-Time PCR Analysis

The RT-IPC nucleic acid molecule was amplified with IPC 5 U and IPC 3L primers using methods known in the art. The RT-PCR kit used for all verification assays was Super-Script™ One-Step RT-PCR with Platinum® Taq DNA polymerase (Invitrogen Life Technologies, Carlsbad, Calif.). All verification experiments were performed on R.A.P.I.D.® (Idaho Technology, Inc., Salt Lake City, Utah).

The effect of the following RT PCR inhibitors, DMSO (Sigma-Aldrich, St. Louis, Mo.), guanidine hydrochloride (Sigma-Aldrich, St. Louis, Mo.), guanidine thiocyanate (Sigma-Aldrich, St. Louis, Mo.), heparin (Sigma-Aldrich, St. Louis, Mo.), SDS (Sigma-Aldrich, St. Louis, Mo.), glycerol (Sigma-Aldrich, St. Louis, Mo.), formamide (Invitrogen Life Technologies, Carlsbad, Calif.), and EDTA (Invitrogen Life Technologies, Carlsbad, Calif.), on the RT-IPC nucleic acid molecule of the present invention was tested. The RT-IPC nucleic acid molecule was titrated to use the smallest amount possible to still obtain consistent results, yet make the assay very sensitive to inhibition.

Using the R.A.P.I.D.® (Idaho Technology, Inc., Salt Lake City, Utah) 1 fg of IPC RNA was found to be optimal for the methods herein. The reagents used were from the Super-Script™ One-Step RT-PCR Kit with Platinum® Taq DNA Polymerase (Invitrogen Life Technologies, Carlsbad, Calif.), which include the 2× reaction mix and 50 mM MgSO₄. The RT-PCR was started with a reverse transcriptase incubation at 50° C. for 15 minutes, followed by a 5-minute reverse transcriptase deactivation/Taq polymerase activation at 95° C. and then 45 cycles of 95° C. for 1 second and 65° C. for 20 seconds. The assay was tested against these eight inhibitors using probes labeled with a reporter dye, FAM. The quencher on the probe was TAMRA. Biosearch Technologies, Novato, Calif., manufactured the probes.

1. DMSO

The effect of DMSO was tested with a 2-fold dilution series from 25% to 0.39% final concentration in a 20 μl reaction volume.

Figure 5:
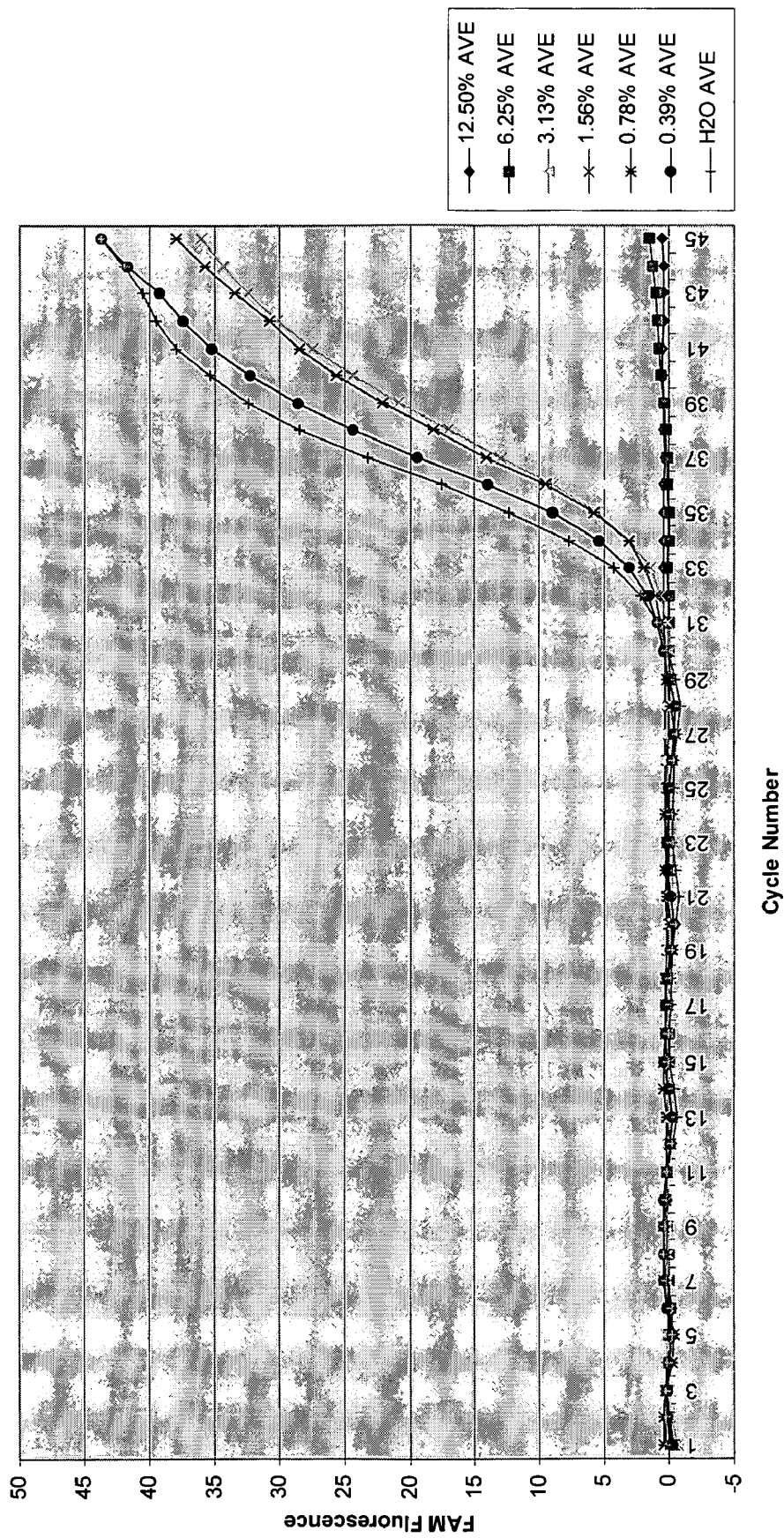

As shown in FIG. 5, DMSO is completely inhibitory at 25% and was partially inhibitory at 6.25%. Inhibition was completely relieved at 3.13%.

2. Guanidine Hydrochloride

The effect of guanidine hydrochloride was tested with a 2-fold dilution series from 200 mM to 3.125 mM final concentration in a 20 μl reaction volume.

Figure 6:
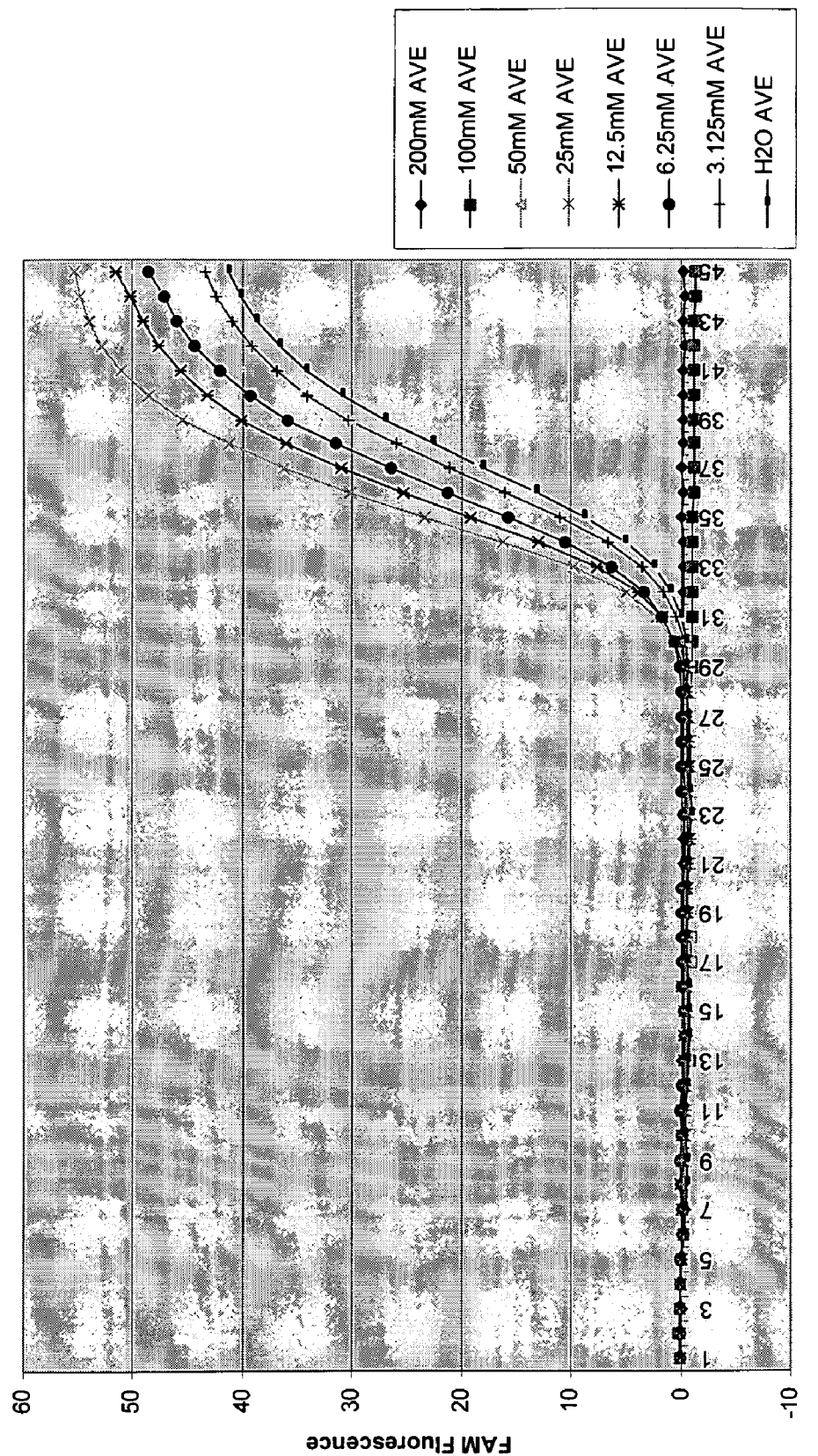

As shown in FIG. 6, Guanidine hydrochloride was completely inhibitory at 200 mM and 100 mM. Inhibition was completely relieved at 50 mM.

3. Guanidine Thiocyanate

The effect of guanidine thiocyanate was tested with a 2-fold dilution series from 100 mM to 3.125 mM final concentration in a 20 μl reaction.

Figure 7:
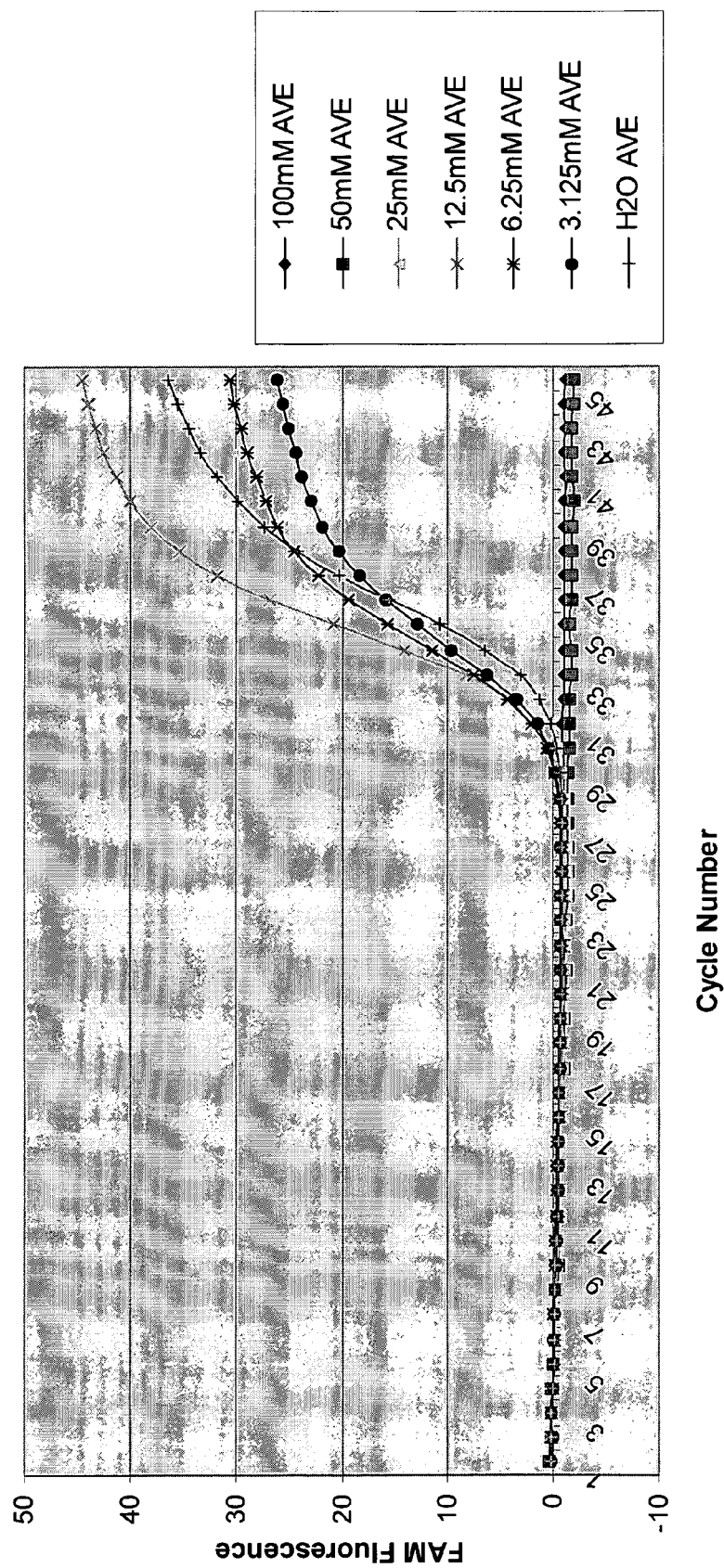

As shown in FIG. 7, Guanidine thiocyanate was completely inhibitory at 100 mM and 50 mM. Inhibition was completely relieved at 25 mM.

4. Heparin

The effect of heparin was tested with a 2-fold dilution series from 0.00125 Units to 0.000156 Units final concentration in a 20 μl reaction.

Figure 8:
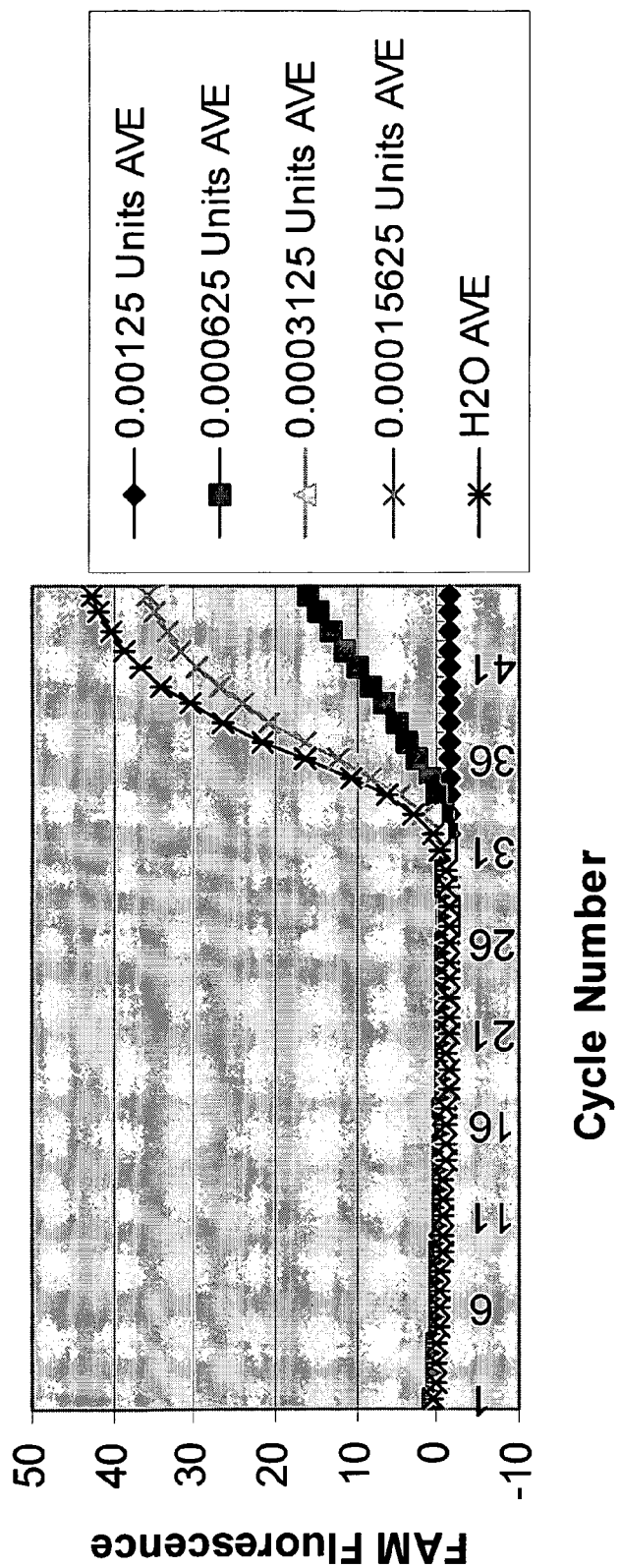

As shown in FIG. 8, heparin was completely inhibitory at 0.00125 Units. Inhibition was completely relieved at 0.000625 Units.

5. SDS

The effect of SDS was tested with 2-fold dilution series from 0.02% to 0.00125% final concentration in a 20 μl reaction.

Figure 9:
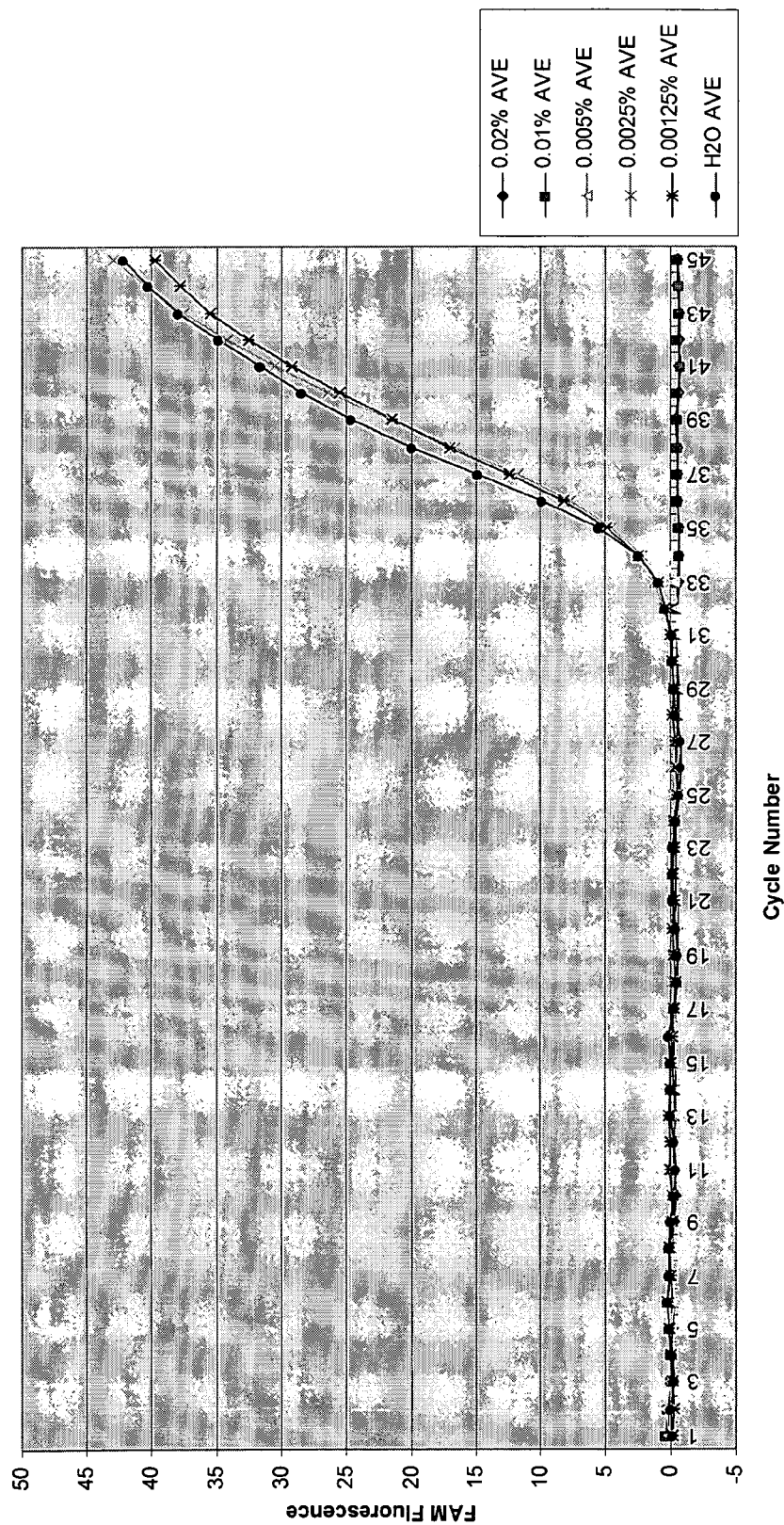

As shown in FIG. 9, SDS was completely inhibitory at 0.02% and 0.01%. Inhibition was completely relieved at 0.005%.

6. Glycerol

The effect of glycerol was tested with a 2-fold dilution series from 25% to 1.56% final concentration in a 20 μl reaction.

Figure 10:
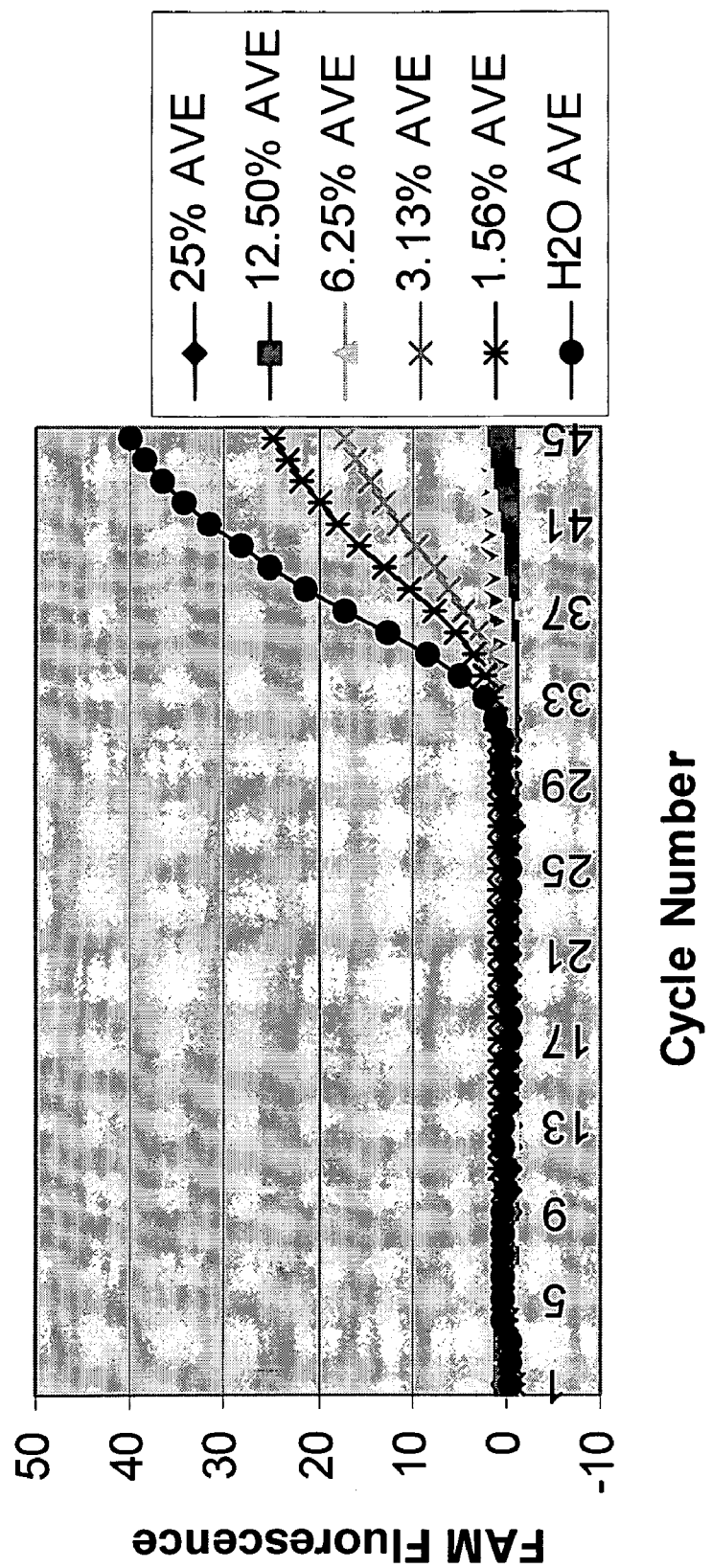

As shown in FIG. 10, glycerol was completely inhibitory at 25%, 12.5%, and 6.25%. At 3.125% glycerol was partially inhibitory and inhibition was not completely relieved until 1.56%.

7. Formamide

The effect of formamide was tested with a 2-fold dilution series from 25% to 0.78% final concentration in a 20 μl reaction.

Figure 11:
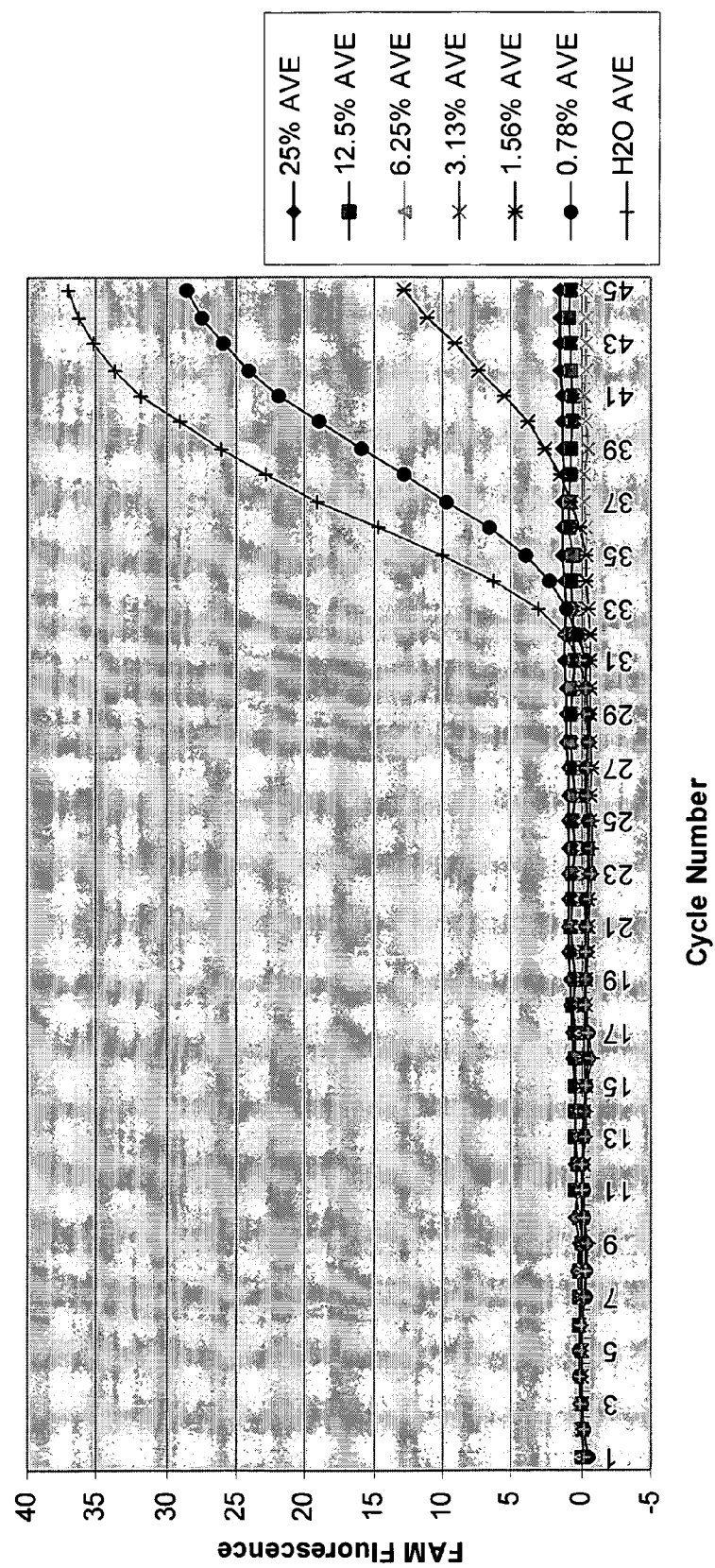

As shown in FIG. 11, formamide was completely inhibitory at 25%, 12.5%, 6.25%, and 3.125%. At 1.56% formamide was partially inhibitory and inhibition was not completely relieved until 0.78%.

8. EDTA

The effect of EDTA was tested with 2-fold dilution series from 5 mM to 0.156 mM final concentration in a 20 μl reaction.

Figure 12:
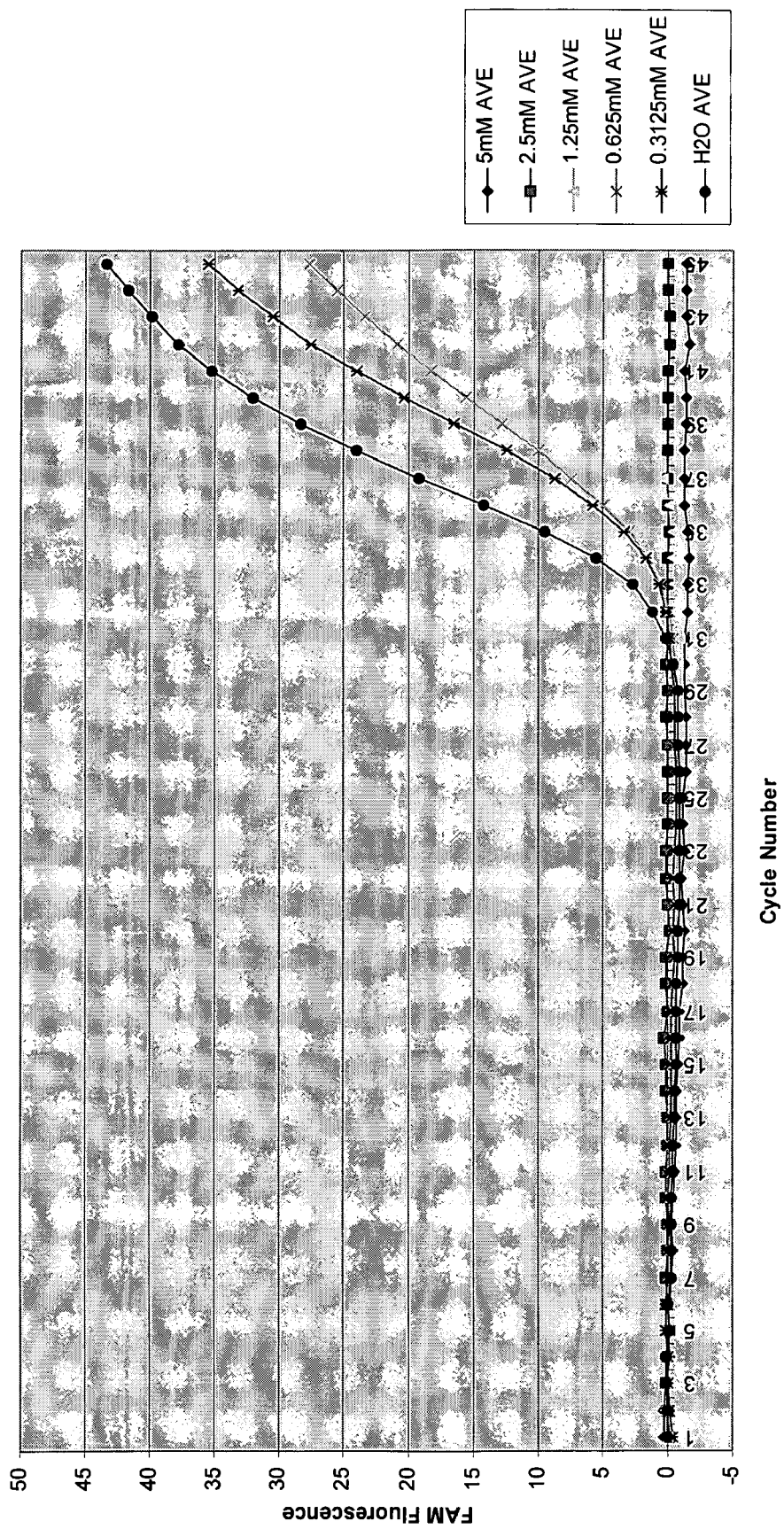

As shown in FIG. 12, EDTA was completely inhibitory at 5 mM and 2.5 mM. At 1.25 mM EDTA was partially inhibitory and inhibition was not completely relieved until 0.625 mM.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. An isolated nucleic acid molecule comprising at least 80 consecutive bases of SEQ ID NO:89 or its complement.

2. A probe comprising the isolated nucleic acid molecule of claim 1 and a label.

3. A probe comprising the isolated nucleic acid molecule of claim 1, a reporter molecule, and a quencher molecule.

4. The probe of claim 3, wherein the reporter molecule produces a signal upon the separation of the reporter molecule and the quencher molecule.

5. The probe of claim 3, wherein the quencher molecule is capable of quenching the signal of the reporter molecule.

6. The probe of claim 3, wherein the reporter molecule is a fluorophore.

7. The probe of claim 6, wherein the fhiorophore is FAM, ROX, Texas Red, TET, TAMRA, JOE, HEX, CAL Red, or VIC.

8. The probe of claim 3, wherein the probe is capable of being cleaved by a protein thereby separating the reporter molecule from the quencher molecule.

9. The probe of claim 8, wherein the protein is Taq polymerase.

10. An assay which comprises contacting the probe of claim 3 with a target nucleic acid molecule.

11. The assay of claim 10, wherein the assay is a nucleic acid hybridization assay.

12. The assay of claim 11, wherein the assay is a TaqMan® based assay.

13. The assay of claim 11, further comprising conducting PCR amplification.

14. The assay of claim 11, further comprising detecting the presence or measuring the amount of the probe and detecting the presence or measuring the amount of a target nucleic acid molecule.

15. The assay of claim 14, wherein the absence of the target nucleic acid molecule and the absence of the probe indicate a true negative result for the target nucleic acid molecule.

16. The assay of claim 14, wherein the absence of the target nucleic acid molecule and the presence of the probe indicate a false negative result for the target nucleic acid molecule.

17. A kit for a probe-based nucleic acid assay comprising the isolated nucleic acid molecule of claim 1 packaged with instructions for use.

18. The kit of claim 17, wherein die isolated nucleic acid molecule contains a label.

19. The kit of claim 18, wherein the label is a reporter molecule and a quencher molecule.

20. The kit of claim 17, wherein the probe-based nucleic acid assay is for the detection of an organism.

21. The kit of claim 17, further comprising reagents or components for detecting the presence of a nucleic acid molecule belonging to the organism.

* * * * *